(12) United States Patent
Inoue et al.

(10) Patent No.: US 7,951,471 B2
(45) Date of Patent: May 31, 2011

(54) ORGANOMETALLIC COMPLEX, AND LIGHT-EMITTING ELEMENT AND LIGHT-EMITTING DEVICE USING THE SAME

(75) Inventors: Hideko Inoue, Atsugi (JP); Satoko Shitagaki, Isehara (JP); Satoshi Seo, Kawasaki (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 979 days.

(21) Appl. No.: 11/792,424

(22) PCT Filed: Dec. 1, 2005

(86) PCT No.: PCT/JP2005/022507
§ 371 (c)(1),
(2), (4) Date: Jun. 6, 2007

(87) PCT Pub. No.: WO2006/062144
PCT Pub. Date: Jun. 15, 2006

(65) Prior Publication Data
US 2008/0113216 A1 May 15, 2008

(30) Foreign Application Priority Data
Dec. 7, 2004 (JP) .................... 2004-353587

(51) Int. Cl.
*H01L 51/54* (2006.01)
*C09K 11/06* (2006.01)
(52) U.S. Cl. .. 428/690; 428/917; 313/504; 257/E51.044
(58) Field of Classification Search .................. None
See application file for complete search history.

(56) References Cited

U.S. PATENT DOCUMENTS

| | | | |
|---|---|---|---|
| 6,303,238 B1 | 10/2001 | Thompson et al. |
| 6,821,645 B2 | 11/2004 | Igarashi et al. |
| 6,821,646 B2 | 11/2004 | Tsuboyama et al. |
| 6,835,469 B2 | 12/2004 | Kwong et al. |
| 6,911,271 B1 | 6/2005 | Lamansky et al. |
| 6,939,624 B2 | 9/2005 | Lamansky et al. |
| 6,953,628 B2 | 10/2005 | Kamatani et al. |
| 7,094,477 B2 | 8/2006 | Kamatani et al. |
| 7,147,935 B2 | 12/2006 | Kamatani et al. |
| 7,220,495 B2 | 5/2007 | Tsuboyama et al. |
| 7,238,437 B2 | 7/2007 | Igarashi et al. |
| 7,238,806 B2 | 7/2007 | Inoue et al. |
| 7,339,317 B2 | 3/2008 | Yamazaki |
| 7,381,479 B2 | 6/2008 | Lamansky et al. |
| 7,400,087 B2 | 7/2008 | Yamazaki |
| 7,413,816 B2 | 8/2008 | Inoue et al. |
| 7,553,560 B2 | 6/2009 | Lamansky et al. |
| 7,771,844 B2 | 8/2010 | Inoue et al. |
| 7,795,429 B2 | 9/2010 | Inoue et al. |
| 2001/0019782 A1 | 9/2001 | Igarashi et al. |
| 2005/0191527 A1 | 9/2005 | Fujii et al. |
| 2005/0242715 A1 | 11/2005 | Inoue et al. |
| 2006/0159955 A1 | 7/2006 | Inoue et al. |
| 2007/0213527 A1 | 9/2007 | Inoue et al. |
| 2007/0241667 A1 | 10/2007 | Ohsawa et al. |
| 2008/0076922 A1 | 3/2008 | Inoue et al. |
| 2008/0281098 A1 | 11/2008 | Lamansky et al. |

FOREIGN PATENT DOCUMENTS

| | | |
|---|---|---|
| EP | 1 348 711 | 10/2003 |
| EP | 1 349 435 | 10/2003 |
| EP | 1574514 A | 9/2005 |
| EP | 1 690 866 | 8/2006 |

(Continued)

OTHER PUBLICATIONS

International Search Report (Application No. PCT/JP2004/018079) dated Apr. 5, 2005, full translation.

(Continued)

*Primary Examiner* — Marie R. Yamnitzky
(74) *Attorney, Agent, or Firm* — Eric J. Robinson; Robinson Intellectual Property Law Office, P.C.

(57) ABSTRACT

It is an object of the present invention to provide a substance capable of emitting phosphorescence. In addition, it is an object of the present invention to provide a light-emitting element that is excellent in chromaticity. One aspect of the present invention is an organometallic complex having a structure represented by a general formula (1). In the general formula (1), $R^1$ to $R^4$ are each any one of hydrogen, a halogen element, an acyl group, an alkyl group, an alkoxyl group, an aryl group, a cyano group, and a heterocyclic group. In addition, $R^5$ to $R^{13}$ are each any one of hydrogen, an acyl group, an alkyl group, an alkoxyl group, an aryl group, a heterocyclic group, and an electron-withdrawing group. An organometallic complex having such a structure can emit phosphorescence with higher emission intensity.

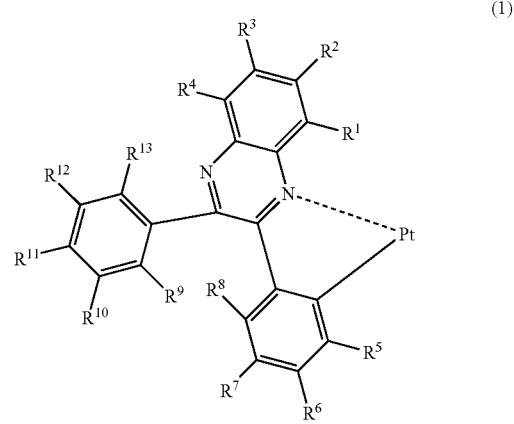

(1)

14 Claims, 17 Drawing Sheets

FOREIGN PATENT DOCUMENTS

| | | |
|---|---|---|
| JP | 63-159856 | 7/1988 |
| JP | 06-207169 | 7/1994 |
| JP | 2001-247859 | 9/2001 |
| JP | 2003-040873 | 2/2003 |
| JP | 2003-058473 | 2/2003 |
| JP | 2004-506305 | 2/2004 |
| JP | 2004-155728 | 6/2004 |
| JP | 2005-239648 | 9/2005 |
| JP | 2006-073992 | 3/2006 |
| JP | 2006-182775 | 7/2006 |
| JP | 3810789 | 8/2006 |
| WO | WO 00/70655 | 11/2000 |
| WO | WO 01/41512 | 6/2001 |
| WO | WO-02/15645 | 2/2002 |
| WO | WO 02/45466 | 6/2002 |
| WO | WO 03/033617 | 4/2003 |
| WO | WO-2004/056839 | 7/2004 |
| WO | WO 2005/054261 | 6/2005 |
| WO | WO 2005/115061 | 12/2005 |

OTHER PUBLICATIONS

Written Opinion (Application No. PCT/JP2004/018079) dated Apr. 5, 2005, full translation.

Search Report (Application No. 04799935.4) dated Jan. 23, 2009.

International Search Report (Application No. PCT/JP2005/022507) dated Feb. 21, 2006.

Written Opinion (Application No. PCT/JP2005/022507) dated Feb. 21, 2006.

M. Kulikova et al., *Effects of the Nature of the Ligand Environment and Metal Center on the Optical and Electrochemical Properties of Platinum(II) and Palladium(II)Ethylenediamine Complexes with Heterocyclic Cyclometalated Ligands*, Russian Journal of General Chemistry, vol. 70, No. 2, 2000, pp. 163-170.

K. Balashev et al., *Synthesis and Properties of Palladium(II) and Platinum(II) (2,3-diphenylquinoxalinato-C,N)ethylenediamine Complexes*, Russian Journal of General Chemistry, vol. 69, No. 8, 1999, pp. 1348-1349.

P. Steel et al., *Cyclometallated Compounds V. Double Cyclopalladation of Diphenyl Pyrazines and Related Ligands*, Journal of Organometallic Chemistry, vol. 395, No. 3, 1990, pp. 359-373.

S. Rasmussen et al., *Synthesis and Characterization of a Series of Novel Rhodium and Iridium Complexes Containing Polypyridyl Bridging Ligands: Potential Uses in the Development of Multimetal Catalysts for Carbon Dioxide Reduction*, Inorganic Chemistry, vol. 29, No. 20; 1990, pp. 3926-3932.

Y. Ito et al., *Asymmetric Synthesis of Helical Poly(quinoxaline-2,3-Diyl)s by Palladium-Mediated Polymerization of 1,2-Diisocyanobenzenes: Effective Control of the Screw-Sense by a Binaphthyl Group at the Chain-End*, Journal of the American Chemical Society, vol. 120, 1998, pp. 11880-11893.

Y. Ito et al., *Living Polymerization of 1, 2-Diisocyanoarenes Promoted by (Quinoxalinyl)nickel Complexes*, Polymer Journal, vol. 24, No. 3, 1992, pp. 297-299.

H. Fujii et al., *Efficient Red Organometallic Phosphors Bearing 2,3-Diphenylquinoxalines and Their Application to Electrophosphorescent Diodes*, Korea-Japan Joint Forum, Organic Materials for Electronics and Photonics, Nov. 3-6, 2004, (04-O).

Tsutsui et al., *High Quantum Efficiency in Organic Light-Emitting Devices with Iridium-Complex as a Triplet Emissive Center*, Japanese Journal of Applied Physics, vol. 38, Part 2, No. 12B, Dec. 15, 1999, pp. L1502-L1504.

D, O'Brien et al., *Improved Energy Transfer in Electrophosphorescent Devices*, Applied Physics Letters, vol. 74, No. 3, Jan. 18, 1999, pp. 442-444.

M. Baldo et al., *High-Efficiency Fluorescent Organic Light-Emitting Devices Using a Phosphorescent Sensitizer*, Nature, vol. 403, Feb. 17, 2000, pp. 750-753.

T. Tsutsui, *The Operation Mechanism and the Light Emission Efficiency of the Organic EL Element*, Textbook of the $3^{rd}$ Seminar at Division of Organic Molecular Electronics and Bioelectronics, The Japan Society of Applied Physics, 1993, pp. 31-37.

M. Thompson et al., *Phosphorescent Materials and Devices*, Proceedings of the $10^{th}$ International Workshop on Inorganic and Organic Electroluminescence (EL'00), Dec. 4-7, 2000, pp. 35-38.

J. Duan et al., *New Iridium Complexes as Highly Efficient Orange-Red Emitters in Organic Light-Emitting Diodes*, Advanced Materials, vol. 15, No. 3, Feb. 5, 2003, pp. 224-228.

G. Zhang et al., *Synthesis and Photoluminescence of a New Red Phosphorescent Iridium(III) Quinoxaline Complex*, Chinese Chemical Letters, vol. 15, No. 11, 2004, pp. 1349-1352.

Fujii.H et al., *Highly Efficient and Vivid-Red Phosphors Bearing 2,3-Diphenylquinoxaline Units and Their Application to Organic Light-Emitting Devices*, IEICE Transactions on Electronics, vol. E87-C, No. 12, Dec. 2004, pp. 2119-2121.

Brooks.J et al., "Synthesis and Characterization of Phosphorescent Cyclometalated Platinum Complexes,"Inorg. Chem. (Inorganic Chemistry), 2002, vol. 41, No. 12, pp. 3055-3066.

Yamamoto et al., "Preparation of New Electron-Accepting π-Conjugated Polyquinoxalines. Chemical and Electrochemical Reduction, Electrically Conducting Properties, and Use in Light-Emitting Diodes," J. Am. Chem. Soc. (Journal of the American Chemical Society), vol. 118, No. 16, 1996, pp. 3930-3937.

Tsutsui et al., "Electroluminescence in Organic Thin Films," Photochemical Processes in Organized Molecular Systems, 1991, pp. 437-450.

Baldo et al., "Highly Efficient Phosphorescent Emission from Organic Electroluminescent Devices," Nature, Sep. 10, 1998, vol. 395, pp. 151-154.

Baldo et al., "Very High-Efficiency Green Organic Light-Emitting Devices Based on Electrophosphorescence," Appl. Phys. Lett. (Applied Physics Letters) Jul. 5, 1999, vol. 75, No. 1, pp. 4-6.

Nishi et al., "High Efficiency TFT-OLED Display with Iridium-Complex as Triplet Emissive Center," Proceedings of the 10th International Workshop on Inorganic and Organic Electroluminescence (EL'00), Dec. 4, 2000, pp. 353-356.

Tang et al., , Appl. Phys. Lett. (Applied Physics Letters) "Organic Electroluminescent Diodes," Sep. 21, 1987, vol. 51, No. 12, pp. 913-915.

International Search Report (Application No. PCT/JP2004/018079) dated Apr. 5, 2005.

Written Opinion (Application No. PCT/JP2004/018079) dated Apr. 5, 2005.

Lewis, Hawley's Condensed Chemical Dictionary, 12th ed., p. 594, (1993).

Jakubke et al., Concise Encyclopedia Chemistry, p. 490, (1993).

International Search Report (Application No. PCT/JP2005/009310) dated Aug. 30, 2005.

Written Opinion (Application No. PCT/JP2005/009310) dated Aug. 30, 2005.

International Search Report (Application No. PCT/JP2005/022593) dated Mar. 14, 2006.

Written Opinion (Application No. PCT/JP2005/022593) dated Mar. 14, 2006.

Seo et al., "P-132: Long-Lived Deeply Red Phosphorescent OLEDs Based on Electrochemically Stable Ir Complexes," SID Digest '05, SID International Symposium Digest of Technical Papers, 2005, vol. 36, pp. 806-809.

Parker, McGraw-Hill Dictionary of Chemical Terms, 3rd ed., 1985, p. 200.

Patani et al., "Bioisosterism: A Rational Approach in Drug Design," Chemical Reviews, vol. 96, No. 8, 1996, pp. 3147-3176.

Full English translation of JP 06-207169 (Jul. 26, 1994).

ORGANOMETALLIC COMPLEX, AND LIGHT-EMITTING ELEMENT AND LIGHT-EMITTING DEVICE USING THE SAME

TECHNICAL FIELD

The present invention relates to a substance capable of emitting light by current excitation, particularly to an organometallic complex that emits light by current excitation. In addition, the present invention relates to a light-emitting element and a light-emitting device with the use of the substance.

BACKGROUND ART

A light-emitting element having a layer containing a luminescent substance between a pair of electrodes, which is used as a pixel, a light source, or the like, is provided for a light-emitting device such as a display device or a lighting system. When current flows between the pair of electrodes in the light-emitting element, fluorescence or phosphorescence is emitted from an excited luminescent substance.

In comparison with fluorescence, theoretically, internal quantum efficiency of phosphorescence is 3 times as much as that of fluorescence in the case of current excitation. Therefore, it is considered that higher luminous efficiency is obtained by using a luminescent substance emitting phosphorescence than using a luminescent substance emitting fluorescence; thus, a substance emitting phosphorescence has been developed.

For example, a metal complex where central metal is iridium is mentioned in Reference 1: Japanese Patent Application Laid-Open No. 2001-247859. According to the reference, this metal complex can be used as a material for a light-emitting element.

DISCLOSURE OF INVENTION

It is an object of the present invention to provide a substance capable of emitting phosphorescence.

The present inventors reached the conclusion on the basis of their committed research findings that an organometallic complex having a structure represented by any one of general formulas (1) and (2) described following can emit phosphorescence. In addition, it is also found that an organometallic complex represented by any one of general formulas (3) and (4) described following can emit phosphorescence.

One aspect of the present invention is an organometallic complex having a structure represented by the general formula (1).

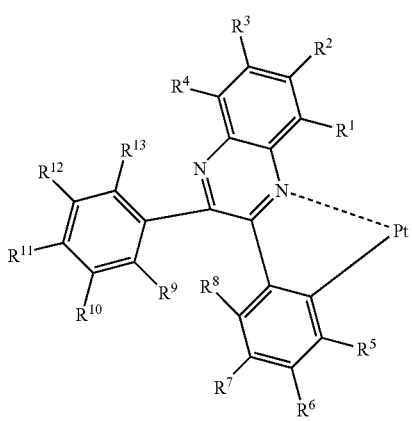

(1)

In the general formula (1), $R^1$ to $R^4$ are each any one of hydrogen, a halogen element, an acyl group, an alkyl group, an alkoxyl group, an aryl group, a cyano group, and a heterocyclic group. In addition, $R^5$ to $R^{13}$ are each any one of hydrogen, an acyl group, an alkyl group, an alkoxyl group, an aryl group, a heterocyclic group, and an electron-withdrawing group. Here, at least one of $R^5$ to $R^{13}$ is preferably an electron-withdrawing group. An organometallic complex having such a structure can emit phosphorescence with higher emission intensity.

Another aspect of the present invention is an organometallic complex having a structure represented by the general formula (2).

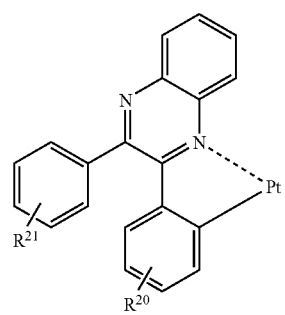

(2)

In the general formula (2), R20 and R21 are each any one of hydrogen, an acyl group, an alkyl group, an alkoxyl group, an aryl group, a heterocyclic group, and an electron-withdrawing group. Here, at least one of R20 and R21 is preferably a group having an electron-withdrawing group. An organometallic complex having such a structure can emit phosphorescence with higher emission intensity.

Another aspect of the present invention is an organometallic complex represented by the general formula (3).

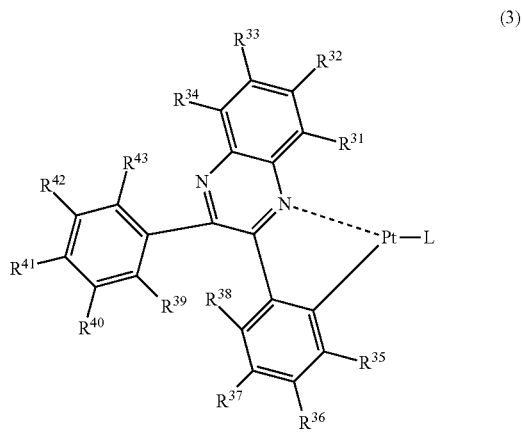

(3)

In the general formula (3), R31 to R34 are each any one of hydrogen, a halogen element, an acyl group, an alkyl group, an alkoxyl group, an aryl group, a cyano group, and a heterocyclic group. In addition, R35 to R43 are each any one of hydrogen, an acyl group, an alkyl group, an alkoxyl group, an aryl group, a heterocyclic group, and an electron-withdrawing group. L represents any one of a monoanionic ligand having a β-diketone structure, a monoanionic bidentate-chelate ligand having a carboxyl group, and a monoanionic bidentate-chelate ligand having a phenolic hydroxyl group. Here, at least one of R35 to R43 is preferably an electron-withdrawing group. An organometallic complex having such a structure can emit phosphorescence with higher emission intensity.

Another aspect of the present invention is an organometallic complex represented by the general formula (4).

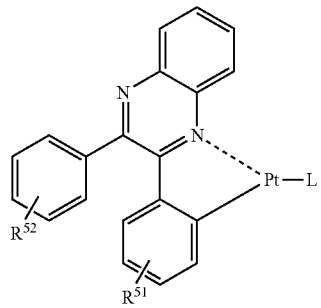
(4)

In the general formula (4), $R^{51}$ and $R^{52}$ are each any one of hydrogen, an acyl group, an alkyl group, an alkoxyl group, an aryl group, a heterocyclic group, and an electron-withdrawing group. Here, at least one of $R^{51}$ and $R^{52}$ is preferably a group having an electron-withdrawing group. An organometallic complex having such a structure can emit phosphorescence with higher emission intensity. In addition, L represents any one of a monoanionic ligand having a β-diketone structure, a monoanionic bidentate-chelate ligand having a carboxyl group, and a monoanionic bidentate-chelate ligand having a phenolic hydroxyl group.

In an organometallic complex having a structure represented by the general formula (1) or (2) or an organometallic complex represented by the general formula (3) or (4), an electron-withdrawing group is preferably any one of a halogen group, a haloalkyl group, and a cyano group. Accordingly, chromaticity of light emitted from the organometallic complex is improved. In addition, a fluoro group is particularly preferable in a halogen group and a trifluoromethyl group is particularly preferable in a haloalkyl group. This improves also the electron trap efficiency of the organometallic complex.

In an organometallic complex represented by the general formula (3) or (4), L is particularly preferable to be monoanionic ligands represented by structural formulas (5) to (11). These monoanionic chelate ligands represented by the structural formulas (5) to (11) have higher in coordination and are available cheaply; thus, the monoanionic chelate ligands are effective.

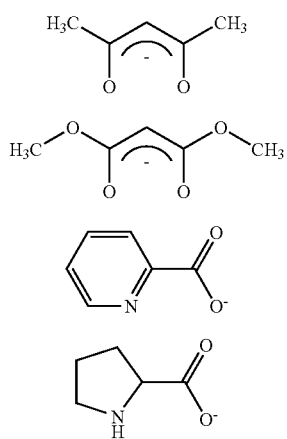

(5)

(6)

(7)

(8)

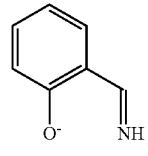
(9)

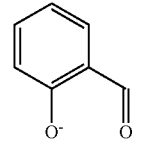
(10)

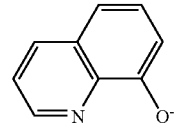
(11)

Another aspect of the present invention is a light-emitting device including a light-emitting element containing an organometallic complex having a structure represented by any one of the general formulas (1) and (2) or an organometallic complex represented by any one of the general formulas (3) and (4).

The other aspect of the present invention is a light-emitting device including a light-emitting element containing an organometallic complex having a structure represented by any one of the general formulas (1) and (2) or an organometallic complex represented by any one of the general formulas (3) and (4).

According to the present invention, an organometallic complex capable of emitting phosphorescence can be obtained. In addition, according to the present invention, an organometallic complex that can be used as a luminescent substance or a sensitizer can be obtained.

By using an organometallic complex according to the present invention as a luminescent substance, a light-emitting element capable of providing red or reddish luminescence having preferable chromaticity can be obtained. In addition, a light-emitting element capable of emitting light efficiently can be obtained by using an organometallic complex according to the present invention as a sensitizer.

BRIEF DESCRIPTION OF DRAWINGS

In the accompanying drawings.

BEST MODE FOR CARRYING OUT THE INVENTION

Figure 1:
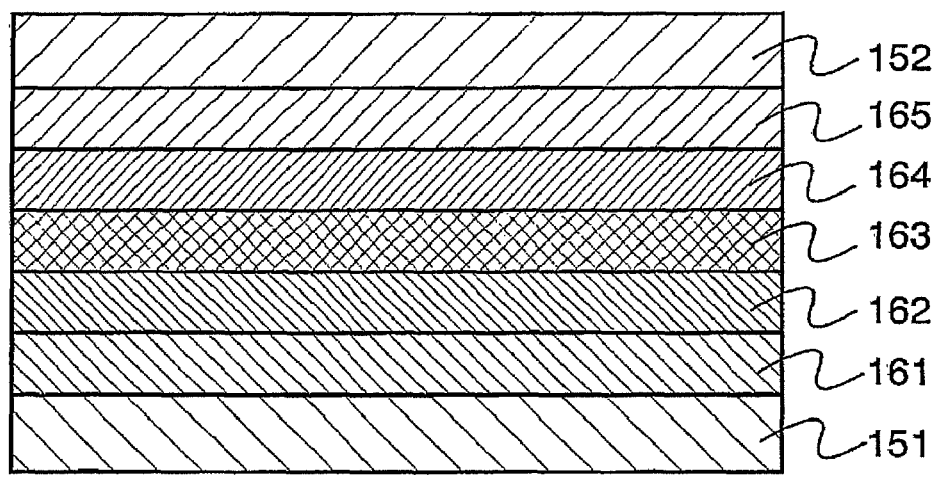
FIG. 1 is a diagram explaining a light-emitting element according to the present invention.

The embodiment modes according to the present invention will hereinafter be described referring to the accompanying drawings. It is easily understood by those who skilled in the art that the embodiment modes and details herein disclosed can be modified in various ways without departing from the purpose and the scope of the present invention. The present invention should not be interpreted as being limited to the description of the embodiment modes to be given below.

Embodiment Mode 1

Organometallic complexes represented by structural formulas (12) to (25) can be given as one mode according to the present invention.

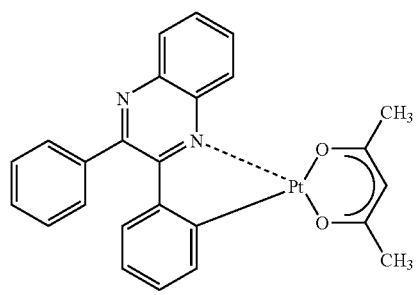
(12)

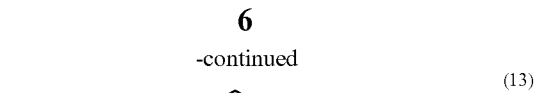
-continued
(13)

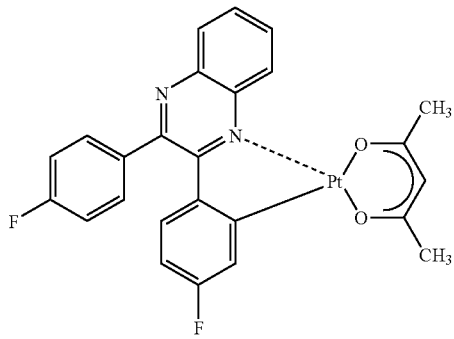

(14)

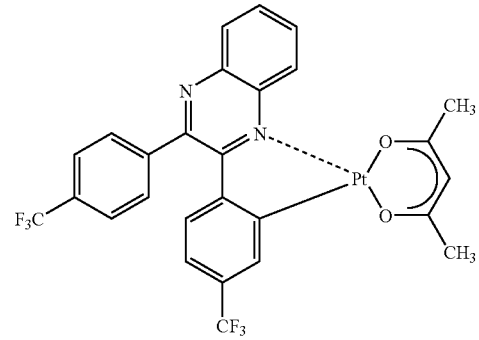

(15)

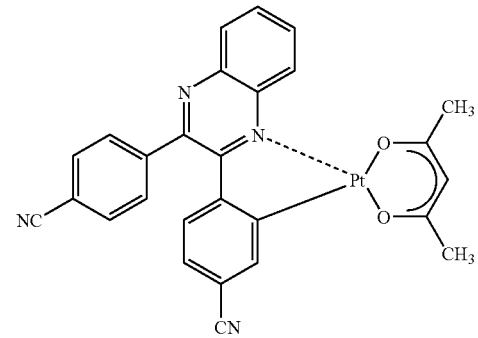

(16)

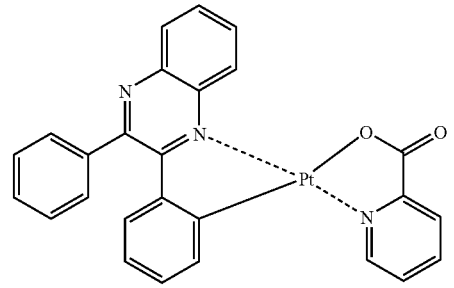

(17)

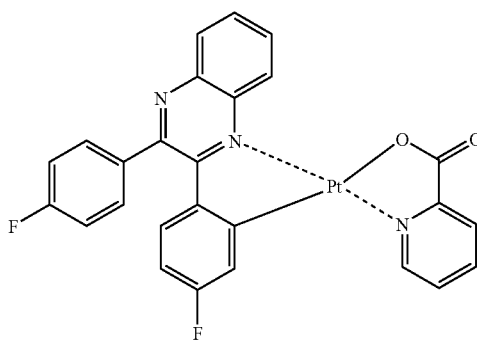

-continued

(18)
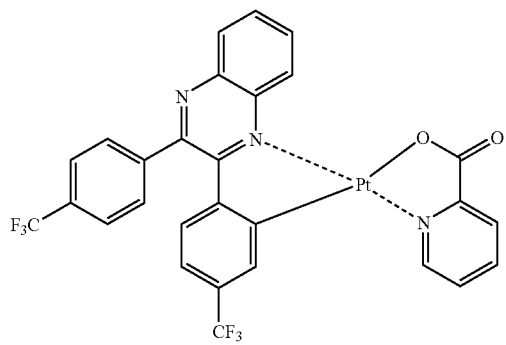

(19)
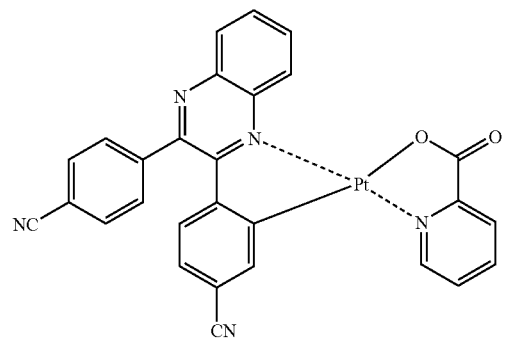

(20)
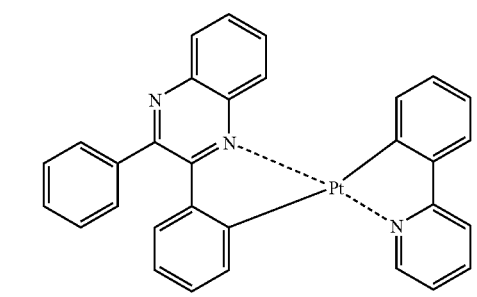

(21)
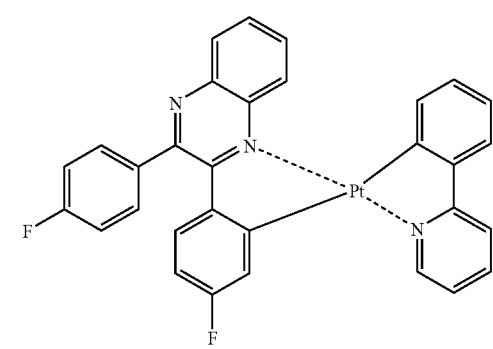

-continued

(22)
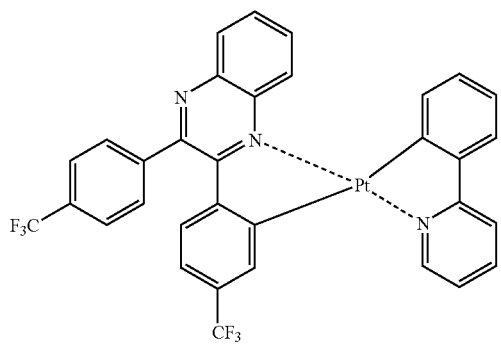

(23)
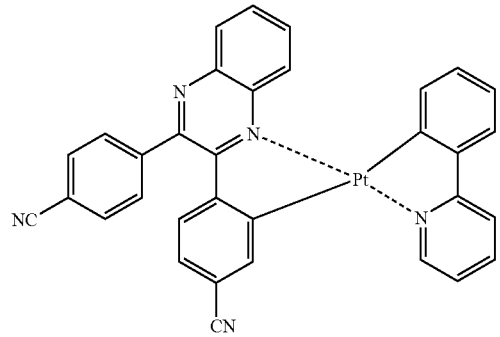

(24)
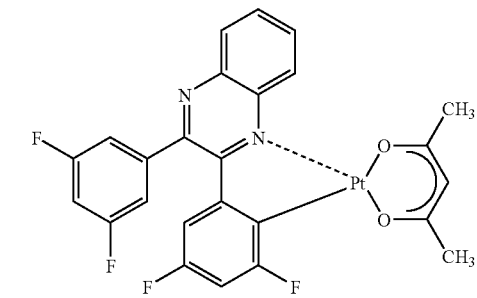

(25)
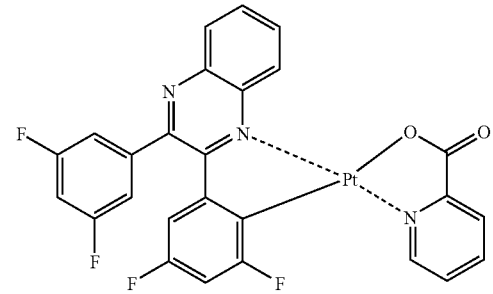

Note that each of fluoro group (represented by —F), trifluoromethyl group (represented by —CF$_3$), and cyano group (represented by —CN) included in an organometallic complex set forth above is an electron-withdrawing group.

Each of organometallic complexes set forth above can emit phosphorescence. In addition, an organometallic complex according to the present invention can be applied to a light-emitting element as a luminescent material. Moreover, an organometallic complex according to the present invention can be applied to a light-emitting element as a photosensitizer.

Embodiment Mode 2

An organometallic complex according to the present invention can be obtained by coordinating a compound A represented by the following general formula (26) with a metal atom by orthometallation reaction. A mode of a synthesis method of an organometallic complex according to the present invention will be explained below.

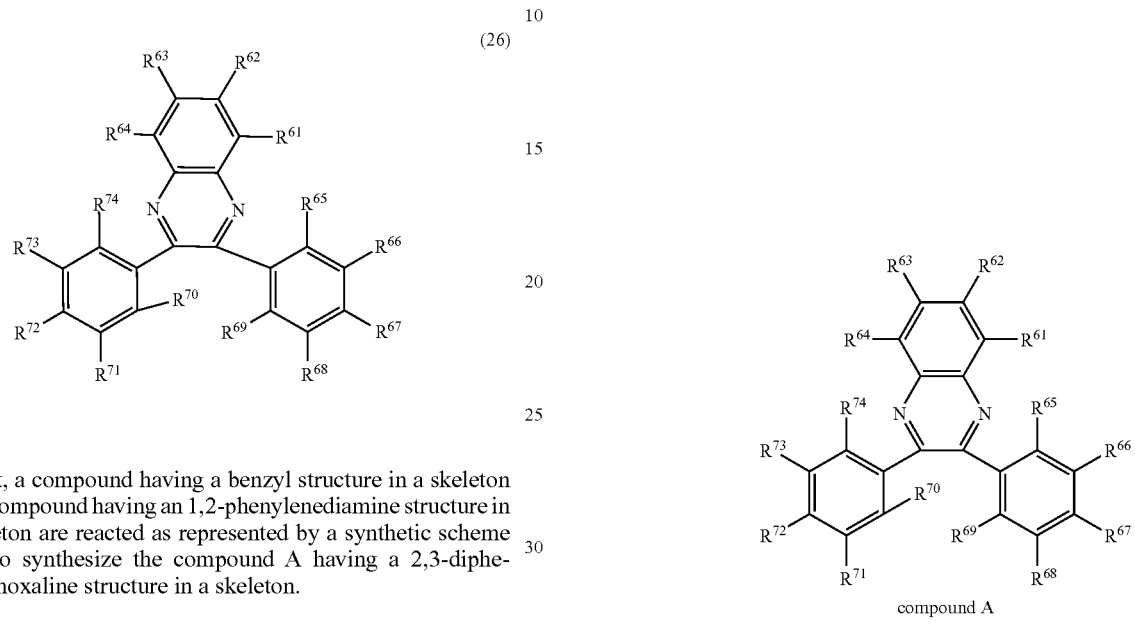

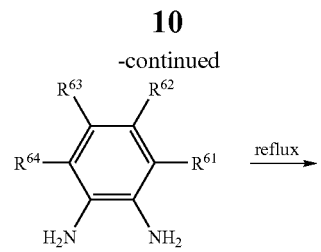

First, a compound having a benzyl structure in a skeleton and a compound having an 1,2-phenylenediamine structure in a skeleton are reacted as represented by a synthetic scheme (a-1) to synthesize the compound A having a 2,3-diphenylquinoxaline structure in a skeleton.

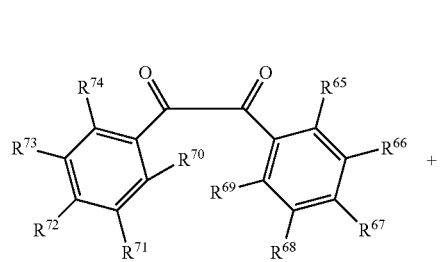

Then, as represented by a synthetic scheme (a-2), the compound A is reacted with a salt containing platinum such as tetrachloroplatinate potassium to synthesize a compound B having a structure where the compound A is coordinated with platinum. The chloro-bridged compound B is also referred to as a dimer complex. The reaction represented by the synthetic scheme (a-2) is referred to as an orthometallation reaction.

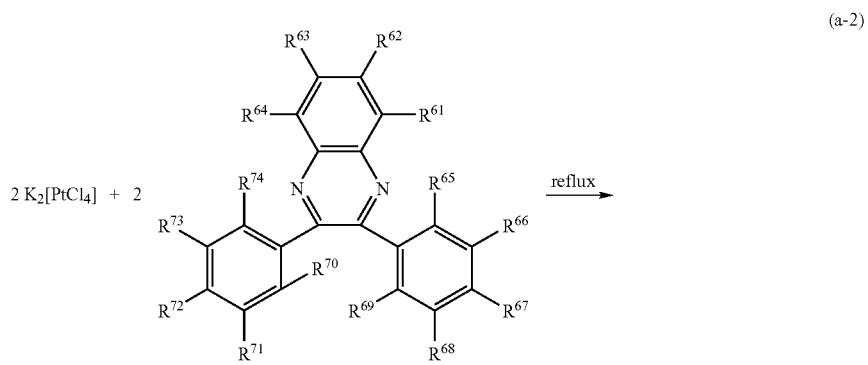

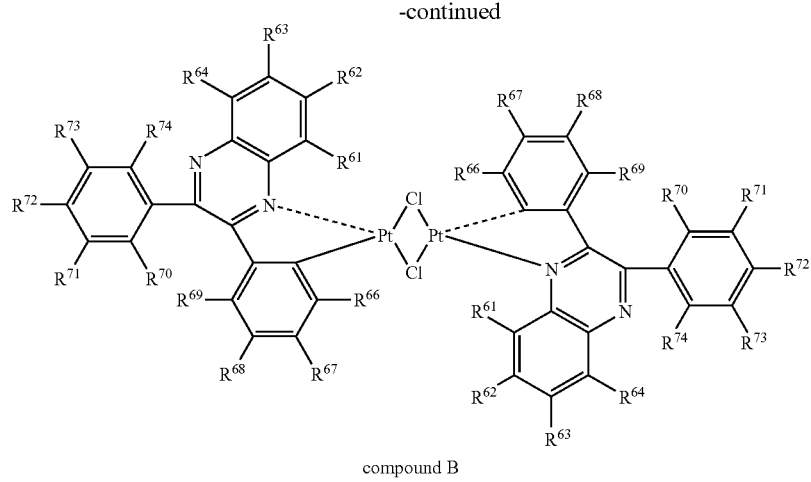
compound B
As represented by a synthetic scheme (a-3), a monoanionic compound is further coordinated with platinum in the compound B to obtain an organometallic complex according to the present invention represented by a general formula (27).
(a-3)
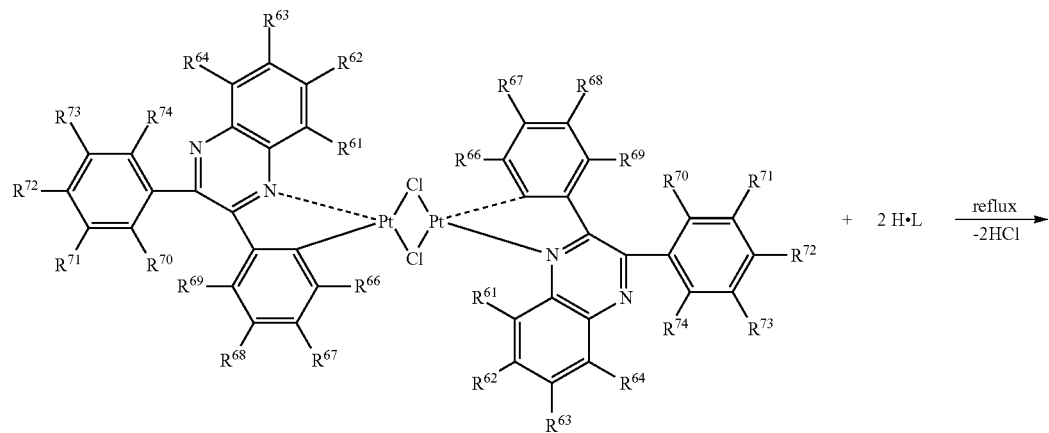
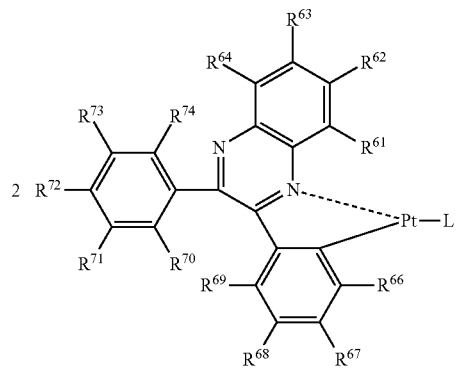

-continued

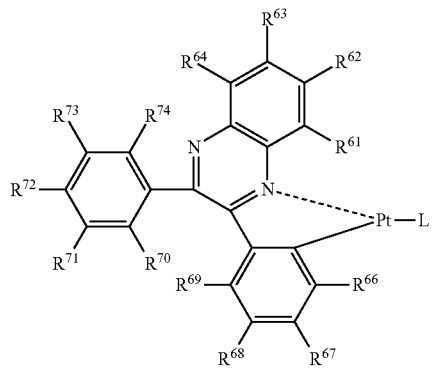

(27)

In the synthetic schemes (a-1), (a-2), and (a-3), and the general formulas (26) and (27), $R^{61}$ to $R^{64}$ are each any one of hydrogen, a halogen element, an acyl group, an alkyl group, an alkoxyl group, an aryl group, and a heterocyclic group. $R^{65}$ to $R^{74}$ are each any one of hydrogen, an acyl group, an alkyl group, an alkoxyl group, an aryl group, a heterocyclic group, and an electron-withdrawing group, and both or any one of $R^{65}$ and $R^{74}$ is hydrogen. In addition, the monoanionic compound is not particularly limited; however, it is preferable to use a compound represented by any one of structural formulas (5) to (11).

Moreover, a compound represented by the general formula (26) can be further substituted for a monoanionic compound coordinated with platinum in the organometallic complex represented by the general formula (27), so that such an organometallic complex according to the present invention that is represented by a general formula (28) can also be obtained.

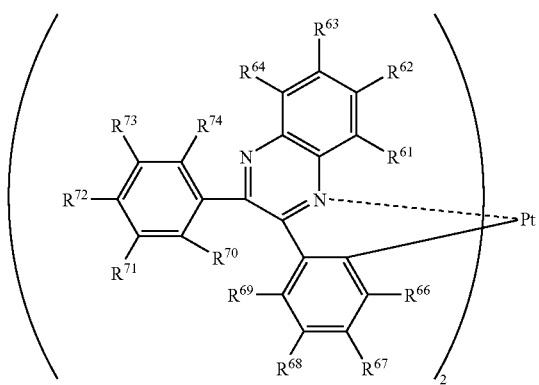

(28)

Embodiment Mode 3

A mode of a light-emitting element in which an organometallic complex according to the present invention is used as a luminescent substance is explained with reference to FIG. 1.

FIG. 1 shows a light-emitting element having a light-emitting layer 163 between a first electrode 151 and a second electrode 152. Then, the light-emitting layer 163 contains an organometallic complex according to the present invention having a structure represented by any one of general formulas (1) and (2) or an organometallic complex according to the present invention represented by any one of general formulas (3) and (4).

In addition to the light-emitting layer 163, a hole-injecting layer 161, a hole-transporting layer 162, an electron-transporting layer 164, an electron-injecting layer 165, and the like are provided between the first electrode 151 and the second electrode 152. When a voltage is applied so that the potential of the first electrode 151 gets higher than that of the second electrode 152, these layers are stacked so that holes are injected from the first electrode 151 side and electrons are injected from the second electrode 152 side.

In such a light-emitting element, the holes injected from the first electrode 151 side and the electrons injected from the second electrode 152 side are recombined in the light-emitting layer 163 and the organometallic complex is made into an excitation state. An organometallic complex according to the present invention in an excited state emits light upon returning to a ground state. Thus, an organometallic complex according to the present invention functions as a luminescent substance.

Here, the light-emitting layer 163 is a layer containing an organometallic complex according to the present invention. The light-emitting layer 163 may be a layer formed only of an organometallic complex according to the present invention. However, when concentration quenching is occurred, the light-emitting layer 163 is preferable to be a layer in which a luminescent substance is mixed to be dispersed in a layer formed of a substance having an energy gap larger than that of a luminescent substance. By containing an organometallic complex according to the present invention in the light-emitting layer 163 by being dispersed, light emission can be prevented from being quenched due to the concentration. Here, the energy gap indicates an energy gap between the LUMO level and the HOMO level.

The substance to be used for dispersing an organometallic complex according to the present invention is not particularly limited. However, a carbazole derivative such as 4,4'-bis(N-carbazolyl)biphenyl (abbreviation: CBP) or 4,4',4"-tris(N-carbazolyl)triphenylamine (abbreviation: TCTA); a metal complex such as bis[2-(2-hydroxyphenyl)pyridinato]zinc (abbreviation: $Znpp_2$), bis[2-(2-hydroxyphenyl)benzoxazolate]zinc (abbreviation: $Zn(BOX)_2$), or tris(8-quinolinolato)aluminum (abbreviation: $Alq_3$); or the like is preferable in addition to a compound having an arylamine skeleton such as 2,3-bis(4-diphenylaminophenyl)quinoxaline (abbreviation: TPAQn) or 4,4'-bis[N-(1-naphthyl)-N-phenylamino]biphenyl (abbreviation: NPB). One or two or more of these substances are selected to be mixed so that an organometallic complex according to the present invention becomes a dispersed state. In addition, an organometallic complex according to the present invention can emit light more efficiently by particularly mixing an organometallic complex according to the present invention and a bipolar substance such as TPAQn. A layer where a plurality of compounds is thus mixed can be formed with the use of a co-evaporation method. Here, co-evaporation refers to an evaporation method in which raw materials are respectively vaporized from a plurality of evaporation sources provided in one treatment chamber, and the vaporized materials are mixed in a gas-phase state to be deposited over a subject.

In addition, the first electrode 151 and the second electrode 152 are not particularly limited and can be formed using gold (Au), platinum (Pt), nickel (Ni), tungsten (W), chromium (Cr), molybdenum (Mo), iron (Fe), cobalt (Co), copper (Cu), palladium (Pd), or the like as well as indium tin oxide (ITO), indium tin oxide containing silicon oxide, or indium oxide formed by using a target mixed with 2 wt. % to 20 wt. % of zinc oxide (ZnO). Moreover, in addition to aluminum, an alloy of magnesium and iron, an alloy of aluminum and lithium, or the like can also be used in forming the first electrode 151. Note that a method for forming the first electrode 151 and the second electrode 152 is not particularly limited and, for example, a sputtering method, a vapor-deposition method, or the like can be used. Note that it is preferable to form one of or both the first electrode 151 and the second electrode 152 by using indium tin oxide or the like or by depositing silver, aluminum, or the like to have a thickness of several nm to several 10 nm so that emitted light can be extracted outside.

Moreover, the hole-transporting layer 162 may be provided between the first electrode 151 and the light-emitting layer 163 as shown in FIG. 1. Here, the hole-transporting layer 162 is a layer having a function to transport the holes injected from the first electrode 151 side to the light-emitting layer 163. By providing the hole-transporting layer 162, the distance between the first electrode 151 and the light-emitting layer 163 can be larger. Consequently, light emission can be prevented from being quenched due to metal contained in the first electrode 151. The hole-transporting layer 162 is preferable to be formed using a substance having high hole transportability and particularly preferable to be formed using a substance having hole mobility of $1 \times 10^{-6}$ cm$^2$/Vs or more. Note that the substance having high hole transportability indicates a substance having higher mobility of holes than that of electrons, where a value of a ratio of hole mobility to electron mobility (=hole mobility/electron mobility) is more than 100. The following can be given as a specific example of a substance that can be used to form the hole-transporting layer 162: 4,4'-bis[N-(1-naphthyl)-N-phenylamino]biphenyl- (abbreviation: NPB); 4,4'-bis[N-(3-methylphenyl)-N-phenylamino]biphenyl (abbreviation: TPD); 4,4',4"-tris(N,N-diphenylamino)triphenylamine (abbreviation: TDATA); 4,4',4"-tris[N-(3-methylphenyl)-N-phenylamino]triphenylamine (abbreviation: MTDATA); 4,4'-bis{N-[4-(N, N-di-m-tolylamino)phenyl]-N-phenylamino}biphenyl (abbreviation: DNTPD); 1,3,5-tris[N,N-di(m-tolyl)amino]benzene (abbreviation: m-MTDAB); 4,4',4"-tris(N-carbazolyl)triphenylamine (abbreviation: TCTA); phthalocyanine (abbreviation: H$_2$Pc); copper phthalocyanine (abbreviation: CuPc); vanadylphthalocyanine (abbreviation: VOPc); and the like. In addition, the hole-transporting layer 162 may also be a multilayer where two or more layers formed of the above substances are combined.

Further, the electron-transporting layer 164 may be provided between the second electrode 152 and the light-emitting layer 163 as shown in FIG. 1. Here, the electron-transporting layer 164 is a layer having a function to transport the electrons injected from the second electrode 152 side to the light-emitting layer 163. By providing the electron-transporting layer 164, the distance between the second electrode 152 and the light-emitting layer 163 can be larger. Consequently, light emission can be prevented from being quenched due to metal contained in the second electrode 152. The electron-transporting layer 164 is preferable to be formed using a substance having high electron transportability and particularly preferable to be formed using a substance having electron mobility of $1 \times 10^{-6}$ cm$^2$/Vs or more. Note that the substance having high electron transportability indicates a substance having higher mobility of electrons than that of holes, where a value of a ratio of electron mobility to hole mobility (=electron mobility/hole mobility) is more than 100. The following can be given as a specific example of a substance that can be used to form the electron-transporting layer 164: -2-(4-biphenylyl)-5-(4-tert-butylphenyl)-1,3,4-oxadiazole- (abbreviation: PBD); -1,3-bis[5-(p-tert-butylphenyl)-1,3,4-oxadiazole-2-yl]benzene- (abbreviation: OXD-7); -3-(4-tert-butylphenyl)-4-phenyl-5-(4-biphenylyl)-1,2,4-triazole- (abbreviation: TAZ); -3-(4-tert-butylphenyl)-4-(4-ethylphenyl)-5-(4-biphenylyl)-1,2,4-triazole- (abbreviation: p-EtTAZ); bathophenanthroline (abbreviation: BPhen); bathocuproin (abbreviation: BCP); 4,4-bis(5-methylbenzoxazol-2-yl)stilbene (abbreviation: BzOs); and the like as well as a metal complex such as tris(8-quinolinolato)aluminum (abbreviation: Alq$_3$); tris(4-methyl-8-quinolinolato)aluminum (abbreviation: Almq$_3$); bis(10-hydroxybenzo[h]-quinolinato)berylium (abbreviation: BeBq$_2$); bis(2-methyl-8-quinolinolato)-4-phenylphenolate-aluminum (abbreviation: BAlq); bis[2-(2-hydroxyphenyl)benzoxazolate]zinc (abbreviation: Zn(BOX)$_2$); and bis[2-(2-hydroxyphenyl)benzothiazorato]zinc (abbreviation: Zn(BTZ)$_2$). In addition, the electron-transporting layer 164 may also be a multilayer where two or more layers formed of the above substances are combined.

Note that the hole-transporting layer 162 and the electron-transporting layer 164 may be each formed by using a bipolar substance in addition to the above substances. The bipolar substance indicates the following substance: when mobility of either carrier of an electron or a hole is compared with mobility of the other carrier, a value of a ratio of one carrier mobility to the other carrier mobility is 100 or less, preferably 10 or less. As for the bipolar substance, for example, 2,3-bis(4-diphenylaminophenyl)quinoxaline (abbreviation: TPAQn); 2,3-bis{4-[N-(1-naphthyl)-N-phenylamino]phenyl}-dibenzo[f,h]quinoxaline (abbreviation: NPADiBzQn); and the like can be given. It is preferable to particularly use a substance of which hole and electron mobility are each $1 \times 10^{-6}$ cm$^2$/Vs or more in the bipolar substance. In addition, the hole-transporting layer 162 and the electron-transporting layer 164 may be formed by using the same bipolar substance.

Furthermore, the hole-injecting layer 161 may be provided between the first electrode 151 and the hole-transporting layer 162 as shown in FIG. 1. The hole-injecting layer 161 is a layer having a function to assist holes to be injected to the hole-transporting layer 162 from the first electrode 151. By providing the hole-injecting layer 161, ionization potential difference between the first electrode 151 and the hole-transporting layer 162 is relieved; thus, holes are easily injected. The hole-injecting layer 161 is preferably formed using a substance of which ionization potential is lower than that of a substance forming the hole-transporting layer 162 and higher than that of a substance forming the first electrode 151 or using a substance of which energy band curves by being provided as a thin film of 1 nm to 2 nm between the hole-transporting layer 162 and the first electrode 151. In other words, the hole-injecting layer 161 can be formed by selecting such a substance of which ionization potential is lower than that of the hole-transporting layer 162. As for a specific example of a substance that can be used to form the hole-injecting layer 161, a phthalocyanine-based compound such as phthalocyanine (abbreviation: $H_2Pc$) or copper phthalocyanine (CuPc), a high molecular weight material such as poly(ethylenedioxythiophene)/poly(styrenesulfonic acid) solution (PEDOT/PSS), and the like can be given.

In addition, the electron-injecting layer 165 may be provided between the second electrode 152 and the electron-transporting layer 164 as shown in FIG. 1. Here, the electron-injecting layer 165 is a layer having a function to assist electrons to be injected to the electron-transporting layer 164 from the second electrode 152. By providing the electron-injecting layer 165, electron affinity difference between the second electrode 152 and the electron-transporting layer 164 is relieved; thus, electrons are easily injected. The electron-injecting layer 165 is preferably formed using a substance of which electron affinity is higher than that of a substance forming the electron-transporting layer 164 and lower than that of a substance forming the second electrode 152 or using a substance of which energy band curves by being provided as a thin film of 1 nm to 2 nm between the electron-transporting layer 164 and the second electrode 152. In other words, the electron-injecting layer 165 can be formed by having higher electron affinity than the electron-transporting layer 164. The following can be given as a specific example of a substance that can be used to form the electron-injecting layer 165: inorganic matter such as alkaline metal, alkaline earth metal, fluoride of alkaline metal, fluoride of alkaline earth metal, oxide of alkaline metal, or oxide of alkaline earth metal. In addition to the inorganic matter, a substance that can be used to form the electron-transporting layer 164 such as BPhen, BCP, p-EtTAZ, TAZ, or BzOs can also be used as a substance for forming the electron-injecting layer 165 by selecting a substance of which electron affinity is larger than that of a substance for forming the electron-transporting layer 164 from these substances.

In a light-emitting element according to the present invention as set forth above, each of the hole-injecting layer 161, the hole-transporting layer 162, the light-emitting layer 163, the electron-transporting layer 164, and the electron-injecting layer 165 may be formed by any one of a vapor-deposition method, an inkjet method, a coating method, and the like. In addition, the first electrode 151 or the second electrode 152 may be formed by any one of a sputtering method, a vapor-deposition method, and the like.

Moreover, a hole-generating layer may be provided instead of the hole-injecting layer 161 or an electron-generating layer may be provided instead of the electron-injecting layer 165.

Here, the hole-generating layer is a layer for generating holes. The hole-generating layer can be formed by mixing a substance having higher mobility of holes than that of electrons with a substance that shows electron acceptability to the substance having higher mobility of holes than that of electrons. In addition, the hole-generating layer can also be formed by mixing at least one substance selected from bipolar substances with a substance that shows electron acceptability to the bipolar substance. Here, as for the substance having higher mobility of holes than that of electrons, the same substance as the substance that can be used to form the hole-transporting layer 162 can be used. Moreover, as for the bipolar substance, the above bipolar substance such as TPAQn can be used. It is preferable to particularly use a substance having a triphenylamine structure in a skeleton among the substance having higher mobility of holes than that of electrons and the bipolar substance. Holes can be generated more easily by using the substance having a triphenylamine structure in a skeleton. Further, as for the substance that shows electron acceptability, it is preferable to use metal oxide such as molybdenum oxide, vanadium oxide, ruthenium oxide, or rhenium oxide.

Further, the electron-generating layer is a layer for generating electrons. The electron-generating layer can be formed by mixing a substance having higher mobility of electrons than that of holes with a substance that shows electron-donating properties to the substance having higher mobility of electrons than that of holes. In addition, the hole-generating layer can also be formed by mixing at least one substance selected from bipolar substances with a substance that shows electron-donating properties to the bipolar substance. Here, as for the substance having higher mobility of electrons than that of holes, the same substance as the substance that can be used to form the electron-transporting layer 164 can be used. Moreover, as for the bipolar substance, the above bipolar substance such as TPAQn can be used. Further, as for the substance that shows electron-donating properties, a substance selected from an alkaline metal group and an alkaline earth metal group, specifically lithium (Li), calcium (Ca), natrium (Na), magnesium (Mg), or the like can be used. In addition, alkaline metal oxide or alkaline earth metal oxide, specifically at least one substance of lithium oxide ($Li_2O$), calcium oxide (CaO), natrium oxide ($Na_2O$), potassium oxide ($K_2O$), magnesium oxide (MgO), and the like can also be used as the substance that shows electron-donating properties. Moreover, alkaline metal fluoride or alkaline earth metal fluoride, specifically at least one substance of lithium fluoride (LiF), cesium fluoride (CsF), calcium fluoride ($CaF_2$), and the like can also be used as the substance that shows electron-donating properties. Further, alkaline metal nitride, alkaline earth metal nitride, or the like, specifically at least one substance of calcium nitride, magnesium nitride, and the like can also be used as the substance that shows electron-donating properties.

A light-emitting element according to the present invention as set forth above uses an organometallic complex according to the present invention; therefore, red light emission that is excellent in chromaticity can be provided. In addition, a light-emitting element according to the present invention is capable of emitting phosphorescence, which has desirable luminous efficiency.

Embodiment Mode 4

A light-emitting element according to the present invention may have a plurality of light-emitting layers. For example, white light can be obtained by providing a plurality of light-emitting layers and composition of light emitted from each light-emitting layer. This embodiment mode explains a mode of a light-emitting element having a plurality of light-emitting layers with reference to FIGS. 2 and 3.

Figure 2:
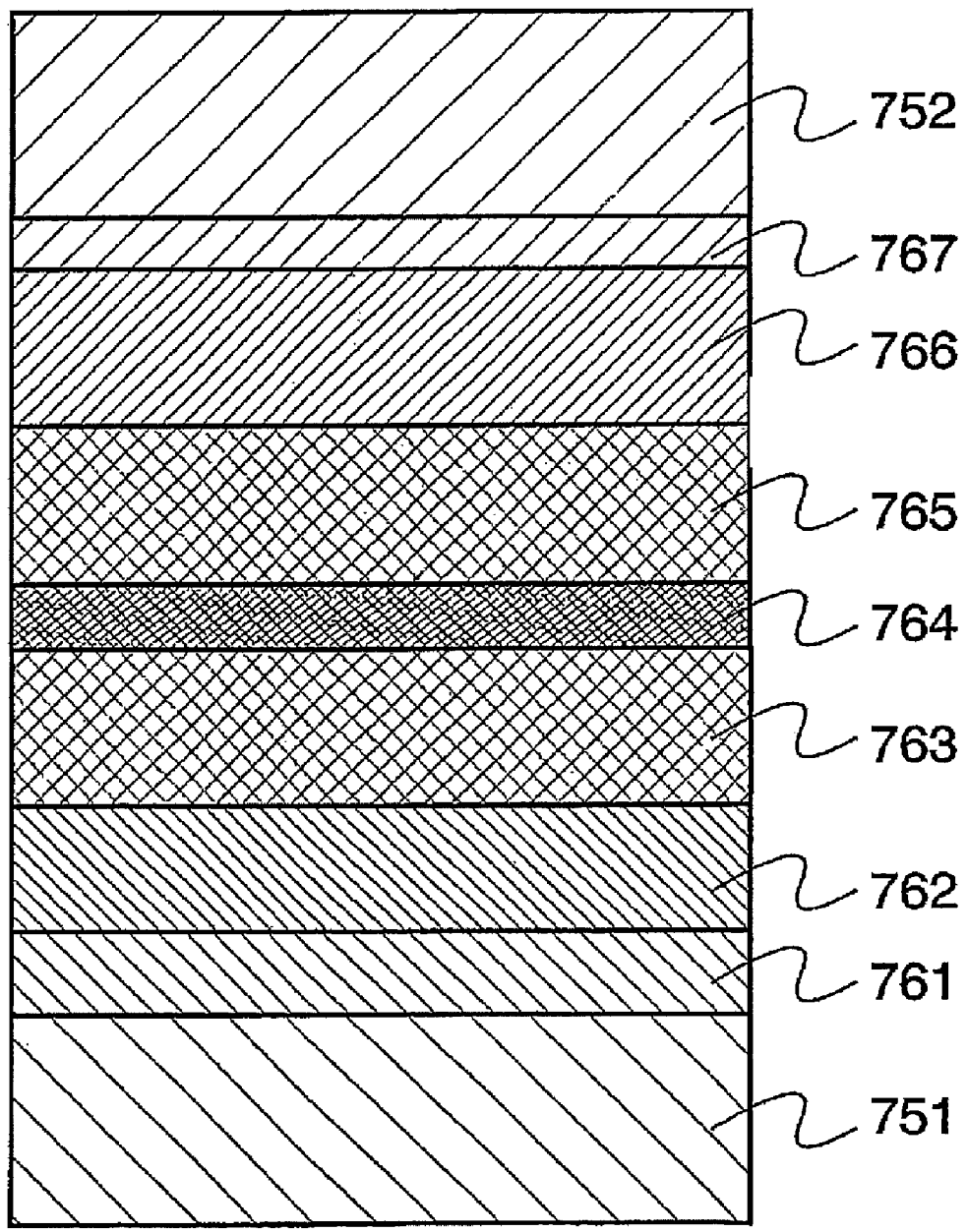
FIG. 2 is a diagram explaining a light-emitting element according to the present invention.

In FIG. 2, a first light-emitting layer 763 and a second light-emitting layer 765 are provided between a first electrode 751 and a second electrode 752. It is preferable to provide an energy-generating layer 764 between the first light-emitting layer 763 and the second light-emitting layer 765.

A current flows between the first electrode 751 and the second electrode 752 when a voltage is applied so that the potential of the first electrode 751 gets lower than the potential of the second electrode 752; thus, holes and electrons are recombined in the first light-emitting layer 763, the second light-emitting layer 765, or the energy-generating layer 764.

Generated excitation energy due to the recombination transfers to each of the first light-emitting layer 763 and the second light-emitting layer 765 from the energy-generating layer 764, and a first luminescent substance contained in the first light-emitting layer 763 and a second luminescent substance contained in the second light-emitting layer 765 are excited. Then, the excited first luminescent substance and second luminescent substance emit light upon each returning to a ground state.

The first light-emitting layer contains a luminescent substance typified by a fluorescence substance such as perylene, 2,5,8,11-tetra-tert-butylperylene (TBP), 4,4'-bis[2,2-diphenylvinyl]biphenyl (DPVBi), 4,4'-bis[2-(N-ethylcarbazole-3-yl)vinyl]biphenyl (BCzVBi), bis(2-methyl-8-quinolinolato)-4-phenylphenolato-aluminum (BAlq), or bis(2-methyl-8-quinolinolato)-chlorogallium (GOamq$_2$Cl), or a phosphorescence substance such as bis[2-(3',5'-bis(trifluoromethyl)phenyl)pyridinato-N,C$^{2'}$]iridium(III)picolinate (Ir(CF$_3$ ppy)$_2$(pic)), bis[2-(4,6-difluorophenyl)pyridinato-N,C$^{2'}$]iridium(III)acetylacetonate (FIr(acac)), or bis[2-(4',6'-difluorophenyl)pyridinato-N,C$^{2'}$]iridium(III)picolinate (FIr(pic)), from which light with a peak at 450 nm to 510 nm in an emission spectrum can be emitted. In addition, the second light-emitting layer 765 contains an organometallic complex according to the present invention so as to serve as a luminescent substance, and light with a peak at 580 nm to 680 nm in an emission spectrum can be emitted from the second light-emitting layer 765. Then, light emitted from the first light-emitting layer 763 and the light emitted from the second light-emitting layer 765 are emitted to the outside through one or both of the first electrode 751 and the second electrode 752. Each light emitted to the outside is composed to be white light.

It is preferable that the first light-emitting layer 763 is a layer in which a luminescent substance capable of providing light-emission of 450 nm to 510 nm is contained to be dispersed in a layer composed of a substance (first host) having a larger energy gap than the luminescent substance, or a layer composed of a luminescent substance capable of providing light-emission of 450 nm to 510 nm. As for the first host, 9,10-di(2-naphthyl)anthracene (abbreviation: DNA), 9,10-di(2-naphthyl)-2-tert-butylanthracene (abbreviation: t-BuDNA), or the like as well as NPB, CBP, TCTA, Znpp$_2$, or Zn(BOX)$_2$ can be used. In addition, it is preferable that the second light-emitting layer 765 is a layer in which an organometallic complex according to the present invention is contained to be dispersed in a layer composed of a substance (second host) having a larger energy gap than the organometallic complex according to the present invention. As for the second host, TPAQn, NPB, CBP, TCTA, Znpp$_2$, Zn(BOX)$_2$, Alq$_3$, or the like can be used. Moreover, it is preferable that the energy-generating layer 764 is formed so that energy generated in the first light-emitting layer 763, the second light-emitting layer 765, or the energy-generating layer 764 can transfer to both the first light-emitting layer 763 and the second light-emitting layer 765, and is formed to have a function for preventing energy from transferring only to one of the first light-emitting layer 763 and the second light-emitting layer 765. Specifically, the energy-generating layer 764 can be formed with the use of TPAQn, NPB, CBP, TCTA, Znpp$_2$, Zn(BOX)$_2$, or the like. By providing the energy-generating layer 764, it is possible to prevent a problem that stronger emission strength from only one of the first light-emitting layer 763 and the second light-emitting layer 765 makes it impossible to obtain white light.

In this embodiment mode, the luminescent substance contained in each of the first light-emitting layer 763 and the second light-emitting layer 765 is not particularly limited. However, as in this embodiment mode, when a luminescent substance which easily traps a carrier is used for a light emitting layer (the second light-emitting layer 765 in this embodiment mode) that is closer to an electrode to serve as an anode (the second electrode 752 in this embodiment mode), the luminescent substance contained in each layer is made to emit light more efficiently.

In addition, in this embodiment mode, the light-emitting element in which the two light-emitting layers are provided as shown in FIG. 2 is described. However, the number of light-emitting layer is not limited to two, and for example, three light-emitting layers may be used. Moreover, light emitted from each light-emitting layer may be composed to be white light.

Further, an electron-transporting layer 762 may be provided between the first light-emitting layer 763 and the first electrode 751 as shown in FIG. 2. In addition to the electron-transporting layer 762, an electron-injecting layer 761 may be provided between the electron-transporting layer 762 and the first electrode 751, a hole-transporting layer 766 may be provided between the second light-emitting layer 765 and the second electrode 752 as shown in FIG. 2, and a hole-injecting layer 767 may be provided between the hole-transporting layer 766 and the second electrode 752.

Figure 3:
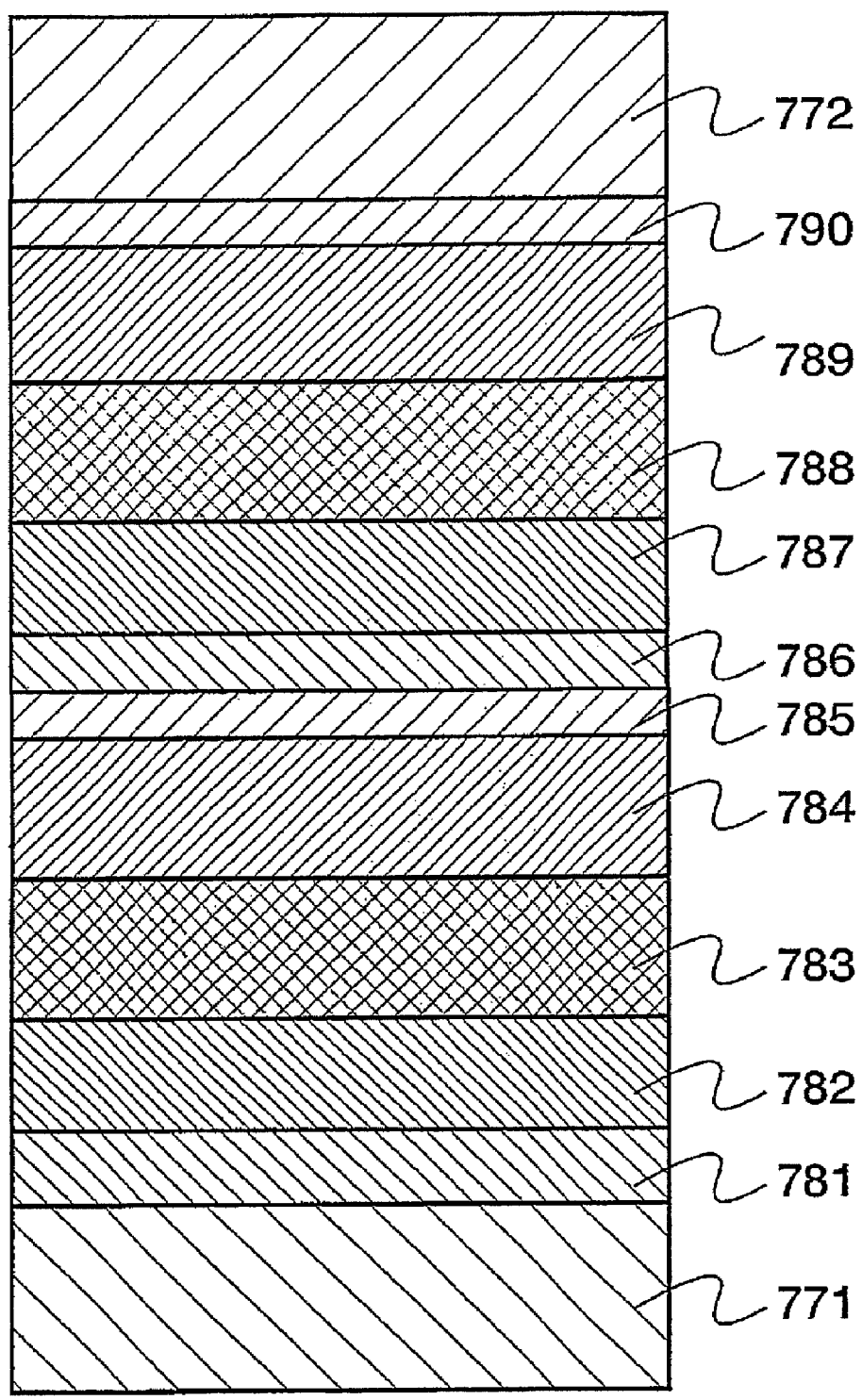
FIG. 3 is a diagram explaining a light-emitting element according to the present invention.

Furthermore, in addition to the light-emitting element mentioned with reference to FIG. 2, a light-emitting element as shown in FIG. 3 may be employed. The light-emitting element of FIG. 3 has a first light-emitting layer 783 and a second light-emitting layer 788 between a first electrode 771 and a second electrode 772. A first layer 785 and a second layer 786 are provided between the first light-emitting layer 783 and the second light-emitting layer 788.

The first layer 785 is a layer for generating holes, and the second layer 786 is a layer for generating electrons. When a voltage is applied so that the potential of the second electrode 772 gets higher than the potential of the first electrode 771, an electron injected from the first electrode 771 and a hole injected from the first layer 785 are recombined in the first light-emitting layer 783, and a luminescent substance contained in the first light-emitting layer 783 emits light. Further, a hole injected from the second electrode 772 and an electron injected from the second layer 786 are recombined in the second light-emitting layer 788, and a luminescent substance contained in the second light-emitting layer 788 emits light.

In the first light-emitting layer 783, an organometallic complex according to the present invention is contained so as to serve as a luminescent substance, and light with a peak at 580 nm to 680 nm in an emission spectrum can be emitted from the first light-emitting layer 783. In addition, the second light-emitting layer 788 contains a luminescent substance typified by a fluorescent substance such as perylene, TBP, DPVBi, BCzVBi, BAlq, or Gamq$_2$Cl, or a phosphorescent substance such as Ir(CF$_3$ ppy)$_2$(pic), FIr(acac), or FIr(pic), from which light with a peak at 450 nm to 510 nm in an emission spectrum can be emitted. Light from the first light-emitting layer 783 and the second light-emitting layer 788 is emitted from one or both of the first electrode 771 and the second electrode 772. Then, the light emitted from each light-emitting layer is composed to be white light.

In the first light-emitting layer 783, it is preferable that an organometallic complex according to the present invention is contained to be dispersed in the first host as set forth above. It is also preferable that the second light-emitting layer 788 is formed in the same way as the second light-emitting layer 788 described above.

It is preferable that the first layer 785 is a layer in which a substance having higher transportability of holes than that of electrons contains a substance that shows electron-acceptability to the substance. As for the substance having higher transportability of holes than that of electrons, the same material as a material that is used for forming a hole-transporting layer may be used. In addition, as for the material that shows electron-acceptability to the substance having higher transportability of holes than that of electrons, molybdenum oxide, vanadium oxide, 7,7,8,8-tetracyanoquinodimethane (abbreviation: TCNQ), 2,3,5,6-tetrafluoro-7,7,8,8-tetracyanoquinodimethane (abbreviation: F4-TCNQ), or the like can be used.

It is preferable that the second layer 786 is a layer in which a substance having higher transportability of electrons than that of holes contains a substance that shows electron-donating properties to the substance. As for the substance having higher transportability of electrons that that of holes, the same material as a material that is used for forming an electron-transporting layer may be used. In addition, as for the material that shows electron-donating properties to the substance having higher transportability of electrons than that of holes, alkali metals such as lithium or cesium, alkali-earth metals such as magnesium or calcium, rare-earth metals such as erbium or ytterbium, or the like can be used.

In addition, an electron-transporting layer 782 may be provided between the first light-emitting layer 783 and the first electrode 771 as shown in FIG. 3, an electron-injecting layer 781 may be provided between the electron-transporting layer 782 and the first electrode 771, a hole-transporting layer 784 may be provided between the first light-emitting layer 783 and the first layer 785, a hole-transporting layer 789 may be provided between the second light-emitting layer 788 and the second electrode 772, a hole-injecting layer 790 may be provided between the hole-transporting layer 789 and the second electrode 772, and an electron-transporting layer 787 may be provided between the second light-emitting layer 788 and the second layer 786.

Note that, for the hole-transporting layer 789, the hole-injecting layer 790, the electron-transporting layer 782, and the electron-injecting layer 781, the same materials as those for the hole-transporting layer 162, the hole-injecting layer 161, the electron-transporting layer 164, and the electron-injecting layer 165 described in Embodiment Mode 3 can be used, respectively. In addition, another functional layer that has a different function from the hole-transporting layer 789, the hole-injecting layer 790, the electron-transporting layer 782, and the electron-injecting layer 781 may be provided.

Moreover, in this embodiment mode, the light-emitting element in which the two light-emitting layers are provided as shown in FIG. 3 is described. However, the number of the light-emitting layer is not limited to two, and for example, three light-emitting layers may be employed. Further, light emitted from each light-emitting layer may be composed to be white light.

Embodiment Mode 5

A mode of a light-emitting element using an organometallic complex according to the present invention as a sensitizer will be explained with reference to FIG. 4.

Figure 4:
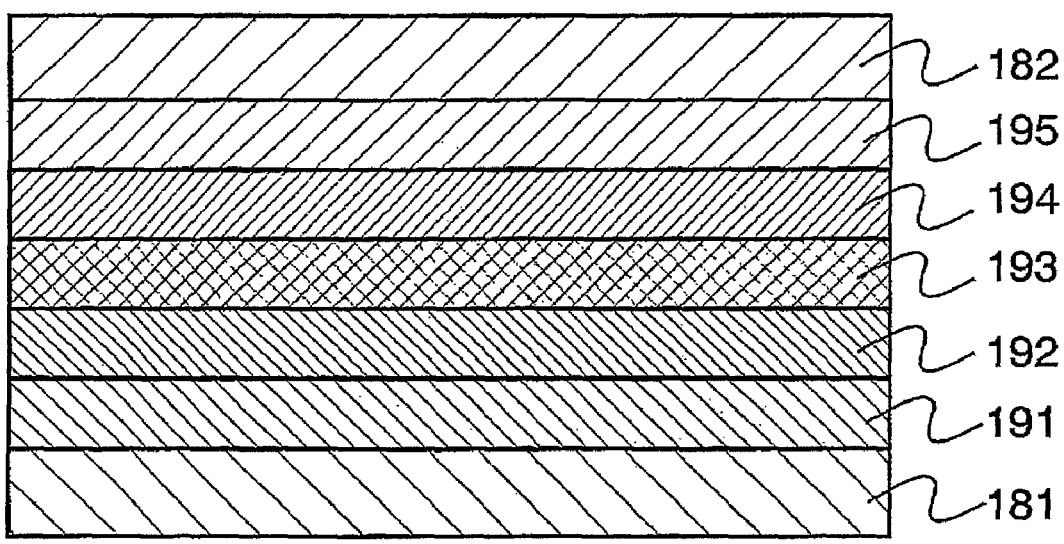
FIG. 4 is a diagram explaining a light-emitting element according to the present invention.

FIG. 4 shows a light-emitting element having a light-emitting layer 193 between a first electrode 181 and a second electrode 182. The light-emitting layer 193 contains an organometallic complex including a structure represented by a general formula (1) or (2) according to the present invention or an organometallic complex represented by a general formula (3) or (4) according to the present invention, and a fluorescent compound capable of providing light-emission of a longer wavelength than the organometallic complex according to the present invention. Here, the fluorescent compound is a substance that emits light upon returning to a ground state from an excited state.

In such a light-emitting element, a hole injected from the first electrode 181 and an electron injected from the second electrode 182 are recombined in the light-emitting layer 193 to bring the fluorescent compound into an excited state. Then, light is emitted upon the fluorescent material in the excited state returning to the ground state. In this case, the organometallic complex according to the present invention acts as a sensitizer for the fluorescent compound to amplify the number of singlet excited states of the fluorescent compound. As set forth above, a light-emitting element that is excellent in luminous efficiency can be obtained by using an organometallic complex according to the present invention as a sensitizer. Note that the first electrode 181 and the second electrode 182 respectively serve as an anode and a cathode in the light-emitting element of this embodiment mode.

Here, the light-emitting layer 193 is not particularly limited. However, it is preferable that the light-emitting layer 193 is a layer in which the organometallic complex according to the present invention and the fluorescent compound are included so as to be dispersed in a layer composed of a substance that has a larger energy gap than the organometallic complex according to the present invention. This makes it possible to prevent quenching of light-emission from the organometallic complex according to the present invention due to the concentration. Note that an energy gap indicates an energy gap between a LUMO level and a HOMO level.

Here, although the fluorescent compound is not particularly limited, compounds that show red to infrared light-emission such as magnesium phthalocyanine or phthalocyanine are preferable.

In addition, the substance to be used for dispersing the organometallic complex according to the present invention and the fluorescent compound is not particularly limited, and the substances that can be used for dispersing the organometallic complex according to the present invention, which are described in Embodiment Mode 3, or the like can be used.

Moreover, the first electrode 181 and the second electrode 182 are not particularly limited, and the same materials as those for the first electrode 151 and second electrode 152 described in Embodiment Mode 3 can be used.

Further, a hole-transporting layer 191, a hole-injecting layer 192, and the like may be provided between the first electrode 181 and the light-emitting layer 193 as shown in FIG. 4, and an electron-transporting layer 194, an electron-injecting layer 195, and the like may be provided also between the second electrode 182 and the light-emitting layer 193.

For the hole-transporting layer 191, the hole-injecting layer 192, the electron-transporting layer 194, and the electron-injecting layer 195, the same materials as those for the hole-transporting layer 162, the hole-injecting layer 161, the electron-transporting layer 164, and the electron-injecting layer 165 described in Embodiment Mode 3 can be used, respectively. In addition, another functional layer that has a different function from the hole-transporting layer 191, the hole-injecting layer 192, the electron-transporting layer 194, and the electron-injecting layer 195 may be provided.

The light-emitting element as set forth above can be obtained by using an organometallic complex according to the present invention as a sensitizer.

Embodiment Mode 6

Since a light-emitting element containing an organometallic complex according to the present invention shows a favorable color of light-emission, a light-emitting device that has a function of displaying favorable images in terms of color can be obtained by using a light-emitting element according to the present invention for a pixel.

In this embodiment mode, a circuit configuration and driving method of a light-emitting device having a display function will be described with reference to FIGS. 5 to 8.

Figure 5:
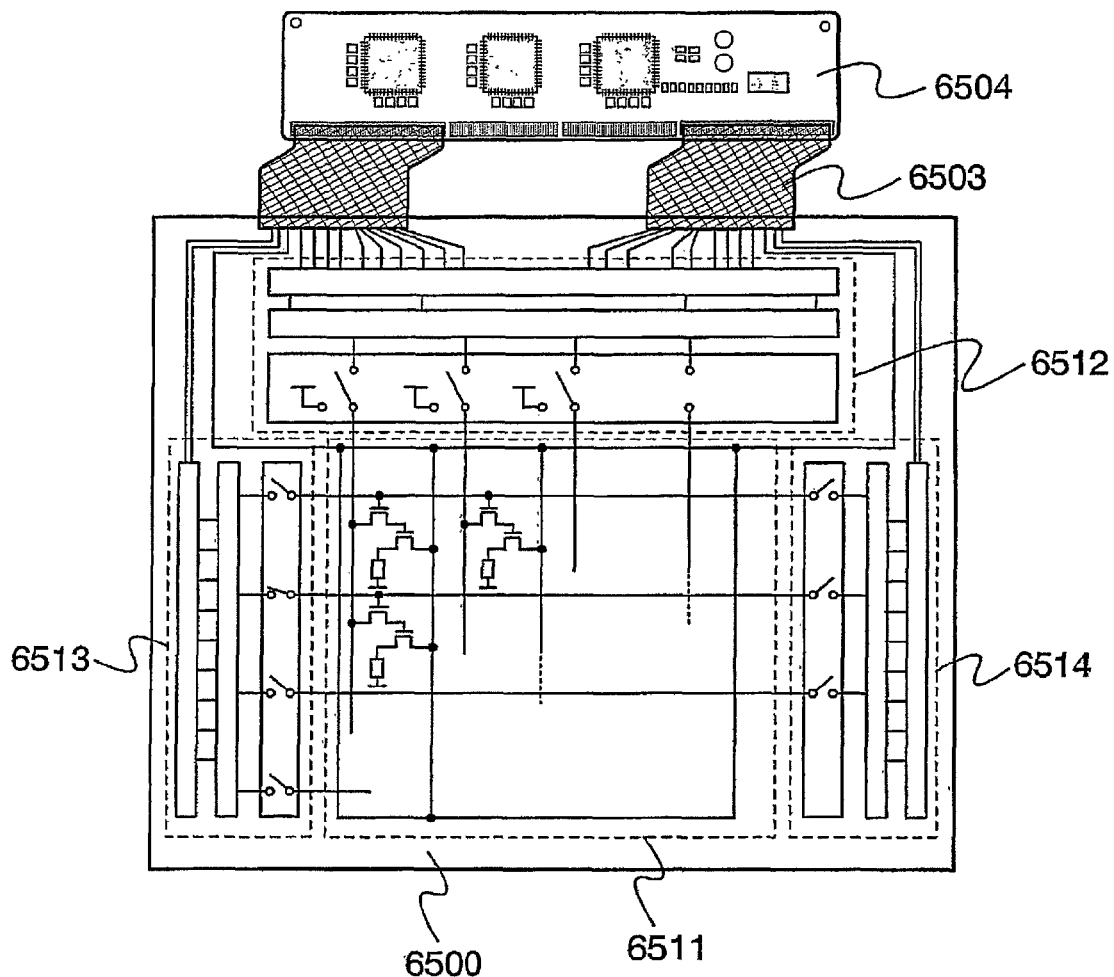
FIG. 5 is a diagram explaining a light-emitting device to which the present invention is applied.

FIG. 5 is an overhead schematic view of a light-emitting device to which the present invention is applied. In FIG. 5, a pixel portion 6511, a source-signal line driver circuit 6512, a writing gate-signal line driver circuit 6513, and an erasing gate-signal line driver circuit 6514 are provided over a substrate 6500. Each of the source-signal line driver circuit 6512, the writing gate-signal line driver circuit 6513, and the erasing gate-signal line driver circuit 6514 is connected to an FPC (flexible printed circuit) 6503 that is an external input terminal through a group of wirings. Further, each of the source-signal line driver circuit 6512, the writing gate-signal line driver circuit 6513, and the erasing gate-signal line driver circuit 6514 receives signals such as a clock signal, a start signal, and a reset signal from the FPC 6503. In addition, a printed wiring board (PWB) 6504 is attached to the FPC 6503. Note that it is not always necessary to provide the driver circuit portion over one substrate over which the pixel portion 6511 is provided as described above. For example, the driver circuit portion may be provided outside the substrate by using a TCP that has an IC chip over an FPC over which a wiring pattern is formed.

In the pixel portion 6511, a plurality of source-signal lines extending in columns is arranged in rows, current-supply lines are arranged to line in rows, and a plurality of gate-signal lines extending in rows is arranged to line in columns. Further, in the pixel portion 6511, a plurality of circuits each including a light-emitting element is arranged.

Figure 6:
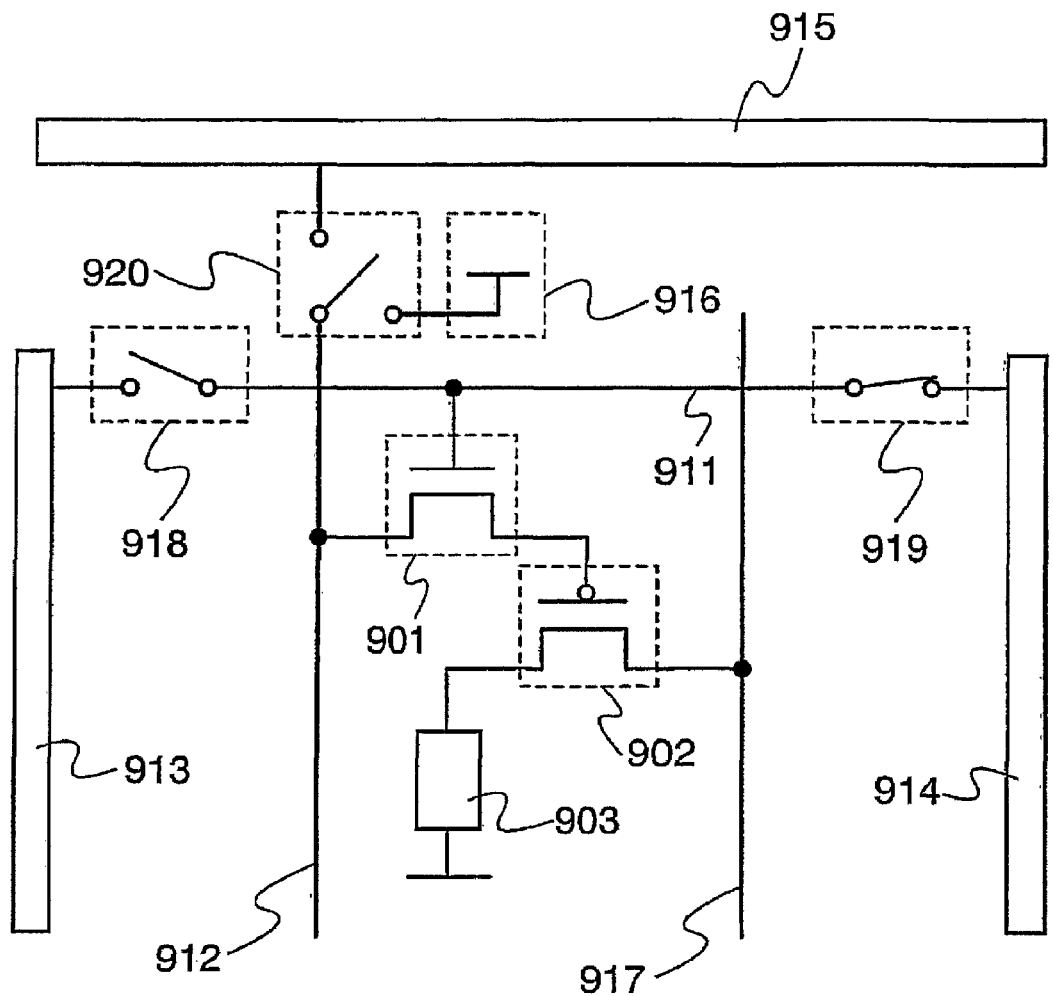
FIG. 6 is a diagram explaining a circuit included in a light-emitting device to which the present invention is applied.

FIG. 6 is a diagram showing a circuit for operating one pixel. The circuit shown in FIG. 6 includes a first transistor 901, a second transistor 902, and a light-emitting element 903.

Each of the first transistor 901 and the second transistor 902 is a three-terminal element including a gate electrode, a drain region, and a source region, and including a channel region between the drain region and the source region. Here, since a source region and a drain region are switched with each other in accordance with a structure or operating conditions of a transistor, it is difficult to identify which one is the drain region or the source region. Consequently, regions that serve as a source or a drain are respectively referred to as a first electrode and a second electrode in this embodiment mode.

A gate-signal line 911 and a writing gate-signal line driver circuit 913 are provided so as to be electrically connected or unconnected by a switch 918, the gate signal line 911 and an erasing gate-signal line driver circuit 914 are provided so as to be electrically connected or unconnected by a switch 919, and a source-signal line 912 is provided so as to be electrically connected to any one of a source-signal line driver circuit 915 and a power source 916 by a switch 920. Further, the first transistor 901 has a gate electrically connected to the gate-signal line 911, a first electrode electrically connected to the source-signal line 912, and a second electrode electrically connected to a gate electrode of the second transistor 902. The second transistor 902 has a first electrode electrically connected to a current-supply line 917 and a second electrode electrically connected to one electrode included in the light-emitting element 903. Note that the switch 918 may be included in the writing gate-signal line driver circuit 913, the switch 919 may be included in the erasing gate-signal line driver circuit 914, and the switch 920 may be included in the source-signal line driver circuit 915.

Figure 7:
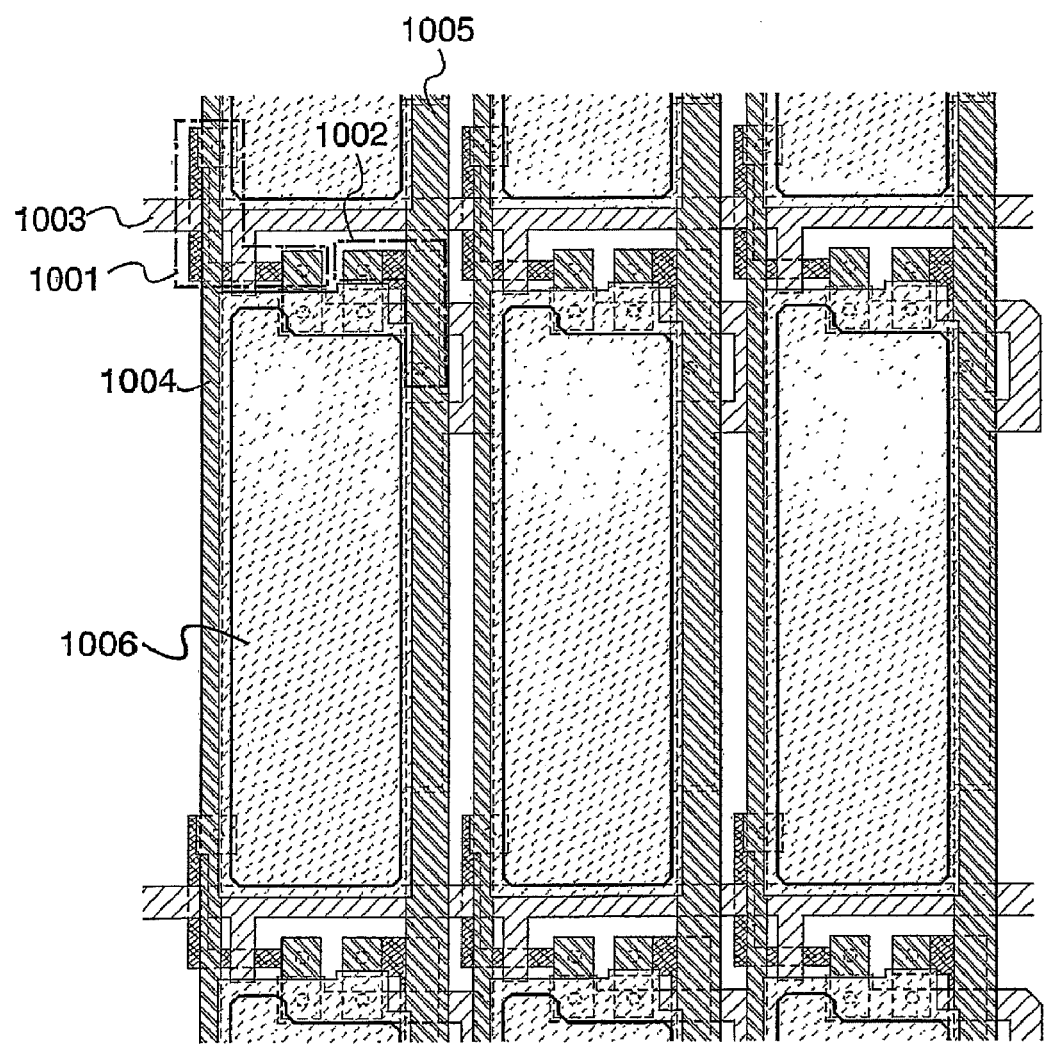
FIG. 7 is a top view of a light-emitting device to which the present invention is applied.

In addition, arrangement of a transistor, a light-emitting element, and the like is not particularly limited. For example, arrangement shown in a top view of FIG. 7 can be employed. In FIG. 7, a first transistor 1001 has a first electrode connected to a source-signal line 1004 and a second electrode connected to a gate electrode of a second transistor 1002. Moreover, the second transistor 1002 has a first electrode connected to a current-supply line 1005 and a second electrode connected an electrode 1006 of a light-emitting element. Part of a gate-signal line 1003 serves as a gate electrode of the first transistor 1001.

Figure 8:
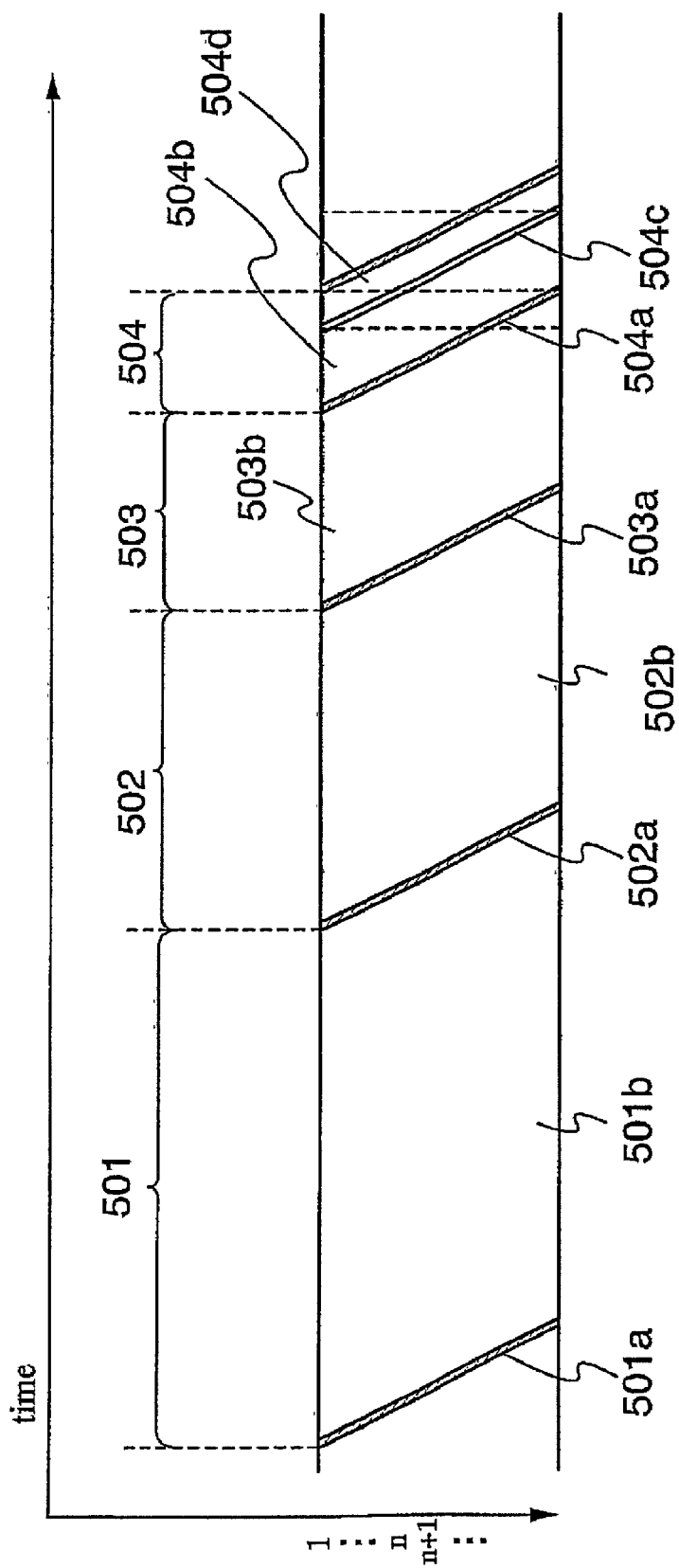
FIG. 8 is a diagram explaining frame operation of a light-emitting device to which the present invention is applied.

Next, a driving method will be explained. FIG. 8 is a diagram illustrating operation per frame with time. In FIG. 8, the horizontal direction indicates passage of time, and the vertical direction indicates ordinal numbers of gate signal lines.

When a light-emitting device according to the present invention is used to display images, rewrite operation and image display operation for a screen are repeated in a display period. Although the number of rewrites is not particularly limited, it is preferable that the number of rewrites be about 60 times per second so as not to make an image viewer recognize flickers. Here, a period for which rewrite operation and display operation are performed for a screen (one frame) is referred to as one frame period.

As shown in FIG. 8, one frame is divided into four sub-frames 501, 502, 503, and 504 respectively including writing periods 501a, 502a, 503a, and 504a and retention periods 501b, 502b, 503b, and 504b. In the retention period, a light-emitting element to which a signal for emitting light is given is made to be in an emitting state. The ratio of the length of the retention period in each sub-frame is first sub-frame 501 to second sub-frame 502 to third sub-frame 503 to fourth sub-frame 504 is $2^3:2^2:2^1:2^0=8:4:2:1$. This makes 4-bit gradation possible. However, the number of bits or the number of gradations is not limited to that described here. For example, eight sub-frames may be provided so as to perform 8-bit gradation.

Operation in one frame will be explained. First, in the sub-frame 501, writing operation is sequentially performed for each of the first row to the last row. Accordingly, the start time of the writing period 501a is different depending on the row. When the writing period 501a is completed, the row is sequentially moved into the retention period 501b. In the retention period 501b, a light-emitting element to which a signal for emitting light is given is made to be in an emitting state. In addition, when the retention period 501b is completed, the row is sequentially moved into the next sub-frame 502, and writing operation is sequentially performed for each of the first row to the last row as in the case of the sub-frame 501. The operation described above is repeated to complete the retention period 504b of the sub-frame 504. When the operation in the sub-frame 504 is completed, the row is moved into the next frame. Thus, the total of time for which light is emitted in each sub-frame is emission time for each light-emitting element in one frame. By varying this emission time with respect to each light-emitting element to have various combinations in one pixel, various different display colors in luminosity and chromaticity can be made.

As in the sub-frame 504, when forcible termination of a retention period of a row for which writing is already completed to move into the retention time is required before writing for the last row is completed, it is preferable that an erasing period 504c is provided after the retention period 504b and a row is controlled so as to be in a non-emitting state forcibly. In addition, the row made to be in the non-emitting state forcibly is kept the non-emitting state for a certain period (this period is referred to as a non-emission period 504d). Then, immediately after the writing period 504a of the last row is completed, the rows are sequentially moved into the next writing period (or the next frame), starting from the first row. This makes it possible to prevent the writing period 504a of the sub-frame 504 from overlapping with the writing period of the next sub-frame.

Although the sub-frames 501 to 504 are arranged in the order of retention period from longest to shortest in this embodiment mode, the arrangement as in this embodiment mode is not always necessary. For example, the sub-frames 501 to 504 may be arranged in the order of retention period from shortest to longest, or may be arranged in random order. In addition, the sub-frames may be divided further into a plurality of frames. In other words, scanning of the gate signal lines may be performed more than once while giving the same image signal.

Now, operation of the circuit shown in FIG. 6 in a writing period and an erasing period will be explained.

First, operation in a writing period will be explained. In the writing period, the n-th (n is a natural number) gate-signal line 911 is electrically connected to the writing gate-signal line driver circuit 913 through the switch 918, and unconnected to the erasing gate-signal line driver circuit 914. In addition, the source-signal line 912 is electrically connected to the source-signal line driver circuit 915 through the switch 920. In this case, a signal is inputted into the gate of the first transistor 901 connected to the n-th (n is a natural number) gate-signal line 911 to turn on the first transistor 901. Then, at this moment, image signals are inputted simultaneously into the first to last source-signal lines 912. Note that the image signals inputted from the respective source-signal lines 912 are independent of each other. The image signal inputted from each of the source-signal lines 912 is inputted into the gate electrode of the second transistor 902 through the first transistor 901 connected to the source-signal line 912. At this moment, a current value supplied to the light-emitting element 903 from the current-supply line 917 depends on the signal inputted into the second transistor 902. Therefore, whether the light-emitting element 903 emits light or not is determined depending on the current value. For example, when the second transistor 902 is a P-channel transistor, the light-emitting element 903 is made to emit light by inputting a Low Level signal to the gate electrode of the second transistor 902. On the other hand, when the second transistor 902 is an N-channel transistor, the light-emitting element 903 is made to emit light by inputting a High Level signal to the gate electrode of the second transistor 902.

Next, operation in an erasing period will be explained. In the erasing period, the n-th (n is a natural number) gate-signal line 911 is electrically connected to the erasing gate-signal line driver circuit 914 through the switch 919 and unconnected to the wiring gate-signal line driver circuit 913. In addition, the source-signal line 912 is electrically connected to the power source 916 through the switch 920. In this case, a signal is inputted into the gate of the first transistor 901 connected to the n-th (n is a natural number) gate-signal line 911 to turn on the first transistor 901. Then, at this moment, erasing signals are inputted simultaneously into the first to last source signal lines 912. The erasing signal inputted from each of the source signal lines 912 is inputted into the gate electrode of the second transistor 902 through the first transistor 901 connected to the source-signal line 912. At this moment, current supply from the current-supply line 917 to the light-emitting element 903 is blocked in accordance with the signal inputted into the second transistor 902. Then, the light-emitting element 903 is forcibly made to be in a non-emitting state. For example, when the second transistor 902 is a P-channel transistor, the light-emitting element 903 is made to emit no light by inputting a High Level signal to the gate electrode of the second transistor 902. On the other hand, when the second transistor 902 is an N-channel transistor, the light-emitting element 903 is made to emit no light by inputting a Low Level signal to the gate electrode of the second transistor 902.

Note that, as for the n-th row (n is a natural number), signals for erasing are inputted by the operation as set forth above in an erasing period. However, as set forth above, the other row (referred to as the m-th row (m is a natural number)) may be in a writing period while the n-th row is in an erasing period. In such a case, it is necessary to input a signal for erasing to the n-th row and input a signal for writing to the m-th row by using the same source signal line. Therefore, operation explained below is preferable.

Immediately after the n-th light-emitting element 903 is made to emit no light by the operation in the erasing period set forth above, the gate-signal line 911 and the erasing gate-signal line driver circuit 914 are made to be unconnected to each other, and the switch 920 is switched to connect the source-signal line 912 and the source-signal line driver circuit 915. Then, in addition to connecting the source-signal line 912 to the source-signal line driver circuit 915, the gate-signal line 911 is connected to the writing gate-signal line driver circuit 913. Then, a signal is inputted selectively into the m-th gate-signal line 911 from the writing gate-signal line driver circuit 913 to turn on the first transistor 901, and signals for writing are inputted into the first to last source signal-lines 912 from the source-signal line driver circuit 915. This signal makes the m-th light-emitting element 903 is made to be in an emitting or non-emitting state.

Immediately after the writing period for the m-th row is completed as set forth above, an erasing period for the (n+1)-th row is started. For that purpose, the gate-signal line 911 and the writing gate-signal line driver circuit 913 are made to be unconnected to each other, and the switch 920 is switched to connect the source-signal line 912 and the power source 916. Further, the gate-signal line 911, which is unconnected to the writing gate-signal line driver circuit 913, is made to be connected to the erasing gate-signal line driver circuit 914. Then, a signal is inputted selectively into the (n+1)-th gate-signal line 911 from the erasing gate-signal line driver circuit 914 to turn on the first transistor 901, and an erasing signal is inputted from the power source 916. Immediately after the erasing period for the (n+1)-th row is thus completed, a writing period for the (m+1)-th row is started. Then, an erasing period and a writing period may be repeated in the same way until an erasing period for the last row is completed.

Although the mode in which the writing period for the m-th row is provided between the erasing period for the n-th row and the erasing period for the (n+1)-th row is explained in this embodiment mode, the present invention is not limited to this. The writing period for the m-th row may be provided between an erasing period for (n−1)-th row and an erasing period for n-th row.

In addition, in this embodiment mode, the operation in which the erasing gate-signal line driver circuit 914 and one gate-signal line 911 are made to be unconnected to each other and the writing gate-signal line driver circuit 913 and the other gate-signal line 911 are made to be connected to each other is repeated as the non-emission period 504*d* is provided in the sub-frame 504. This type of operation may be performed in a frame in which a non-emission period is not particularly provided.

Embodiment Mode 7

One mode of a cross section of a light-emitting device including a light-emitting element according to the present invention will be described with reference to FIGS. 9A to 9C.

Figure 9A:
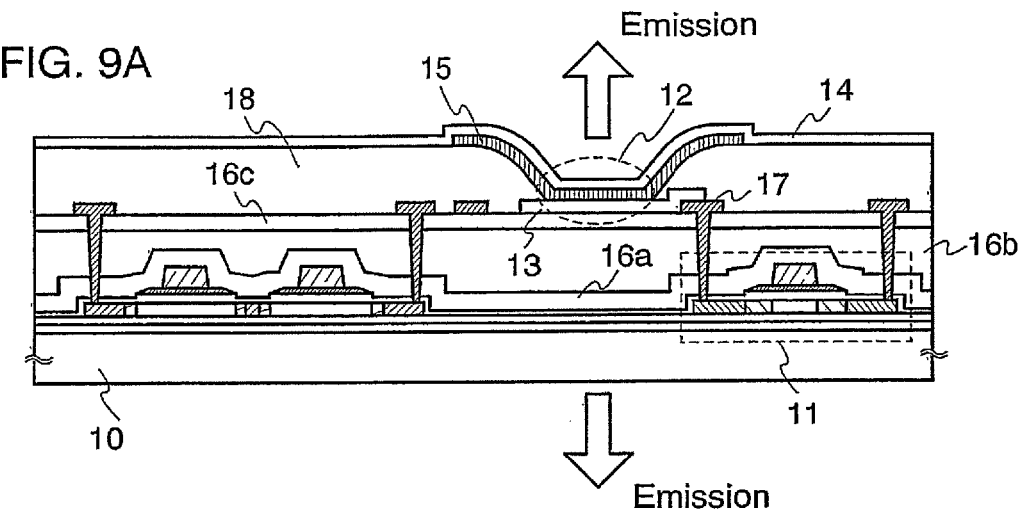
FIGS. 9A to 9C are cross-sectional views of a light-emitting device to which the present invention is applied.
Figure 9B:
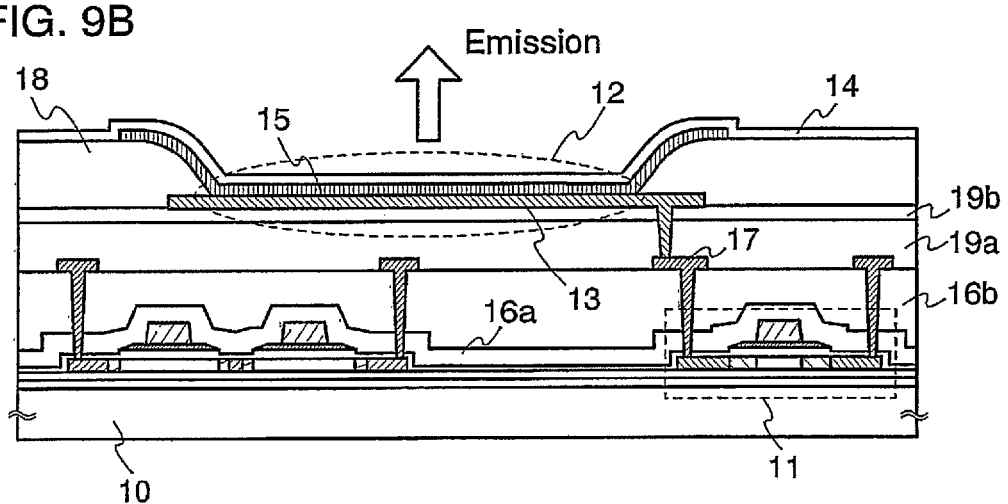
Figure 9C:
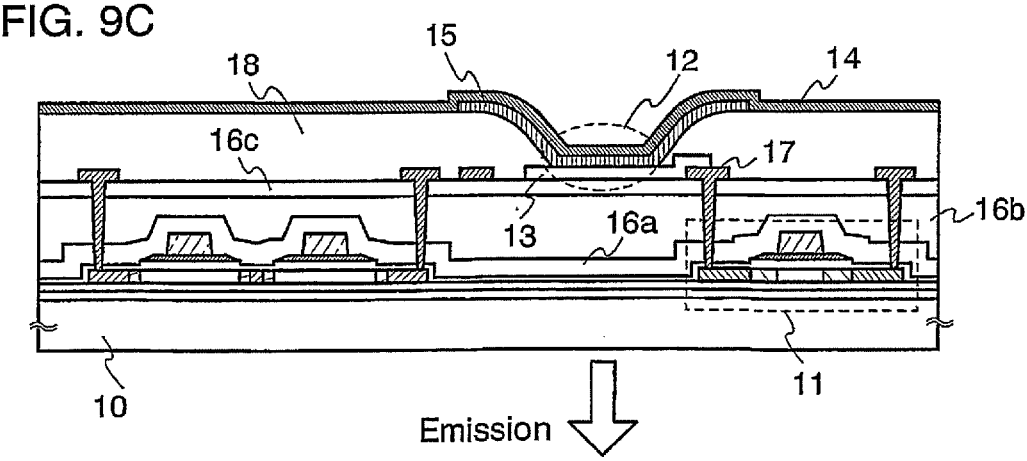

In each of FIGS. 9A to 9C, a portion surrounded by a dotted line is a transistor 11 provided for driving a light-emitting element 12 according to the present invention. The light-emitting element 12 is a light-emitting element according to the present invention, which has a layer 15 in which a layer for generating holes, a layer for generating electrons, and a layer containing a luminescent substance are stacked between a first electrode 13 and a second electrode 14. A drain of the transistor 11 and the first electrode 13 are electrically connected to each other by a wiring 17 running through a first interlayer insulating film 16 (16*a*, 16*b*, and 16*c*). In addition, the light-emitting element 12 is separated by a partition layer 18 from another light-emitting element provided adjacently. A light-emitting device having such a structure according to the present invention is provided over a substrate 10.

Note that the transistor 11 shown in each of FIGS. 9A to 9C is a top-gate TFT in which a gate electrode is provided on the opposite side of a substrate as a center from a semiconductor layer. However, the structure of the transistor 11 is not particularly limited. For example, a bottom-gate TFT may be used. In the case of a bottom-gate TFT, a TFT where a protective film is formed over a semiconductor layer that forms a channel (a channel-protected TFT) may be employed, or a TFT where part of a semiconductor layer that forms a channel is concave (a channel-etched TFT) may be employed.

In addition, a semiconductor layer for forming the transistor 11 may be either crystalline or amorphous, or alternatively, may be semi-amorphous or the like.

The following will describe a semi-amorphous semiconductor. The semi-amorphous semiconductor is a semiconductor that has an intermediate structure between amorphous and crystalline (such as single-crystal or polycrystalline) structures and has a third state that is stable in terms of free energy, which includes a crystalline region that has short range order and lattice distortion. Further, a crystal grain from 0.5 nm to 20 nm is included in at least a region in a film of the semi-amorphous semiconductor. Raman spectrum of the semi-amorphous semiconductor is shifted to a lower wavenumber side less than 520 cm$^{-1}$. The diffraction peaks of (111) and (220), which are believed to be derived from silicon crystal lattice, are observed in the semi-amorphous semiconductor by the X-ray diffraction. The semi-amorphous semiconductor contains hydrogen or halogen of at least 1 atomic % or more for terminating dangling bonds. The semi-amorphous semiconductor is also referred to as a so-called microcrystalline semiconductor. The semi-amorphous semiconductor is formed by glow discharge decomposition with a gas selected from $SiH_4$, $Si_2H_6$, $SiH_2Cl_2$, $SiHCl_3$, $SiCl_4$, $SiF_4$, and the like (using plasma CVD). Each of these gases may also be diluted with $H_2$, or a mixture of $H_2$ and one or more of rare gas elements of He, Ar, Kr, and Ne. The dilution ratio is set to be in the range of 1:2 to 1:1,000. The pressure is set to be approximately in the range of 0.1 Pa to 133 Pa. The power frequency is set to be 1 MHz to 120 MHz, preferably, 13 MHz to 60 MHz. The substrate heating temperature may be set to be 300° C. or less, more preferably, 100° C. to 250° C. As for impurity elements contained in the film, each concentration of impurities for atmospheric constituents such as oxygen, nitrogen and carbon is preferably set to be $1 \times 10^{20}/cm^3$ or less. In particular, the oxygen concentration is set to be $5 \times 10^{19}/cm^3$ or less, preferably, $1 \times 10^{19}/cm^3$ or less.

Moreover, specific examples of crystalline semiconductors for the semiconductor layer include single-crystal or polycrystalline silicon and silicon-germanium, which may be formed by laser crystallization or may be formed by crystallization with solid-phase growth using an element such as nickel.

In the case of using an amorphous substance, for example, amorphous silicon to form the semiconductor layer, it is preferable that the light-emitting device have a circuit in which the transistor 11 and the other transistor (a transistor forming the circuit for driving the light-emitting element) are all N-channel transistors. Other than that case, the light-emitting device may have a circuit including one of an N-channel transistor and a P-channel transistor or may have a circuit including both an N-channel transistor and a P-channel transistor.

Further, the first interlayer insulating film 16 may be a multilayer as shown in FIGS. 9A and 9C, or may be a single layer. Note that the first interlayer insulating film 16*a* includes inorganic matter such as silicon oxide or silicon nitride, and the first interlayer insulating film 16*b* includes a substance with self-flatness such as acrylic, siloxane, or silicon oxide that can be formed by being coated. Note that siloxane has a framework structure formed by the bond between silicon (Si) and oxygen (O), in which an organic group (for example, an alkyl group or an aromatic hydrocarbon group) including at least hydrogen is used as a substituent. As a substituent, a fluoro group may also be used, or an organic group including at least hydrogen and a fluoro group may also be used. In addition, the first interlayer insulating film 16*c* has a silicon nitride film including argon (Ar). Note that the substances included in the respective layers are not particularly limited; therefore, substances other than the substances mentioned here may be used. Moreover, a layer including a substance other than these substances may be combined. In this way, both of inorganic matter and organic matter, or one of inorganic matter and organic matter may be used to form the first interlayer insulating film 16.

As for a partition layer 18, it is preferable that an edge portion have a shape varying continuously in curvature radius. In addition, a substance such as acrylic, siloxane, resist, or silicon oxide is used to form the partition layer 18. One or both of inorganic matter and organic matter may be used to form the partition layer 18.

In each of FIGS. 9A and 9C, only the first interlayer insulating film 16 is provided between the transistor 11 and the light-emitting element 12. However, as shown in FIG. 9B, a second interlayer insulating film 19 (19*a* and 19*b*) may be provided in addition to the first interlayer insulating film 16 (16*a* and 16*b*). In the light-emitting device shown in FIG. 9B, the first electrode 13 is connected to the wiring 17 through the second interlayer insulating film 19.

The second interlayer insulating film 19 may be a multilayer or a single layer in the same way as the first interlayer insulating film 16. The second interlayer insulating film 19*a* includes a substance with self-flatness such as acrylic, siloxane, or silicon oxide that can be formed by being coated. Note that siloxane has a framework structure formed by the bond between silicon (Si) and oxygen (O), in which an organic group (for example, an alkyl group or an aromatic hydrocarbon group) including at least hydrogen is used as a substituent. As a substituent, a fluoro group may also be used, or an organic group including at least hydrogen and a fluoro group may also be used. In addition, the second interlayer insulating film 19b has a silicon nitride film including argon (Ar). The substances included in the respective layers are not particularly limited; therefore, substances other than the substances mentioned here may be used. Moreover, a layer including a substance other than these substances may be combined. In this way, both of inorganic matter and organic matter, or one of inorganic matter and organic matter may be used to form the second interlayer insulating film 19.

In the light-emitting element 12, in the case where both the first electrode 13 and the second electrode 14 are formed by using a light-transmitting substance, emitted light can be extracted from both the first electrode 13 side and the second electrode 14 side as indicated by outline arrows of FIG. 9A. In the case where only the second electrode 14 is formed by using a light-transmitting material, emitted light can be extracted from only the second electrode 14 side as indicated by an outline arrow of FIG. 9B. In this case, it is preferable that the first electrode 13 includes a highly reflective material or that a film composed of a highly reflective material (a reflective film) is provided below the first electrode 13. In the case where only the first electrode 13 is formed by using a light-transmitting substance, emitted light can be extracted from only the first electrode 13 side as indicated by an outline arrow of FIG. 9C. In this case, it is preferable that the second electrode 14 includes a highly reflective material or that a reflective film is provided above the second electrode 14.

In addition, the layer 15 may be stacked so that the light-emitting element 12 operates when a voltage is applied so that the potential of the second electrode 14 is higher than the potential of the first electrode 13, or the layer 15 may be stacked so that the light-emitting element 12 operates when a voltage is applied so that the potential of the second electrode 14 is lower than the potential of the first electrode 13. The transistor 11 is an N-channel transistor in the former case, and the transistor 11 is a P-channel transistor in the latter case.

Figure 11:
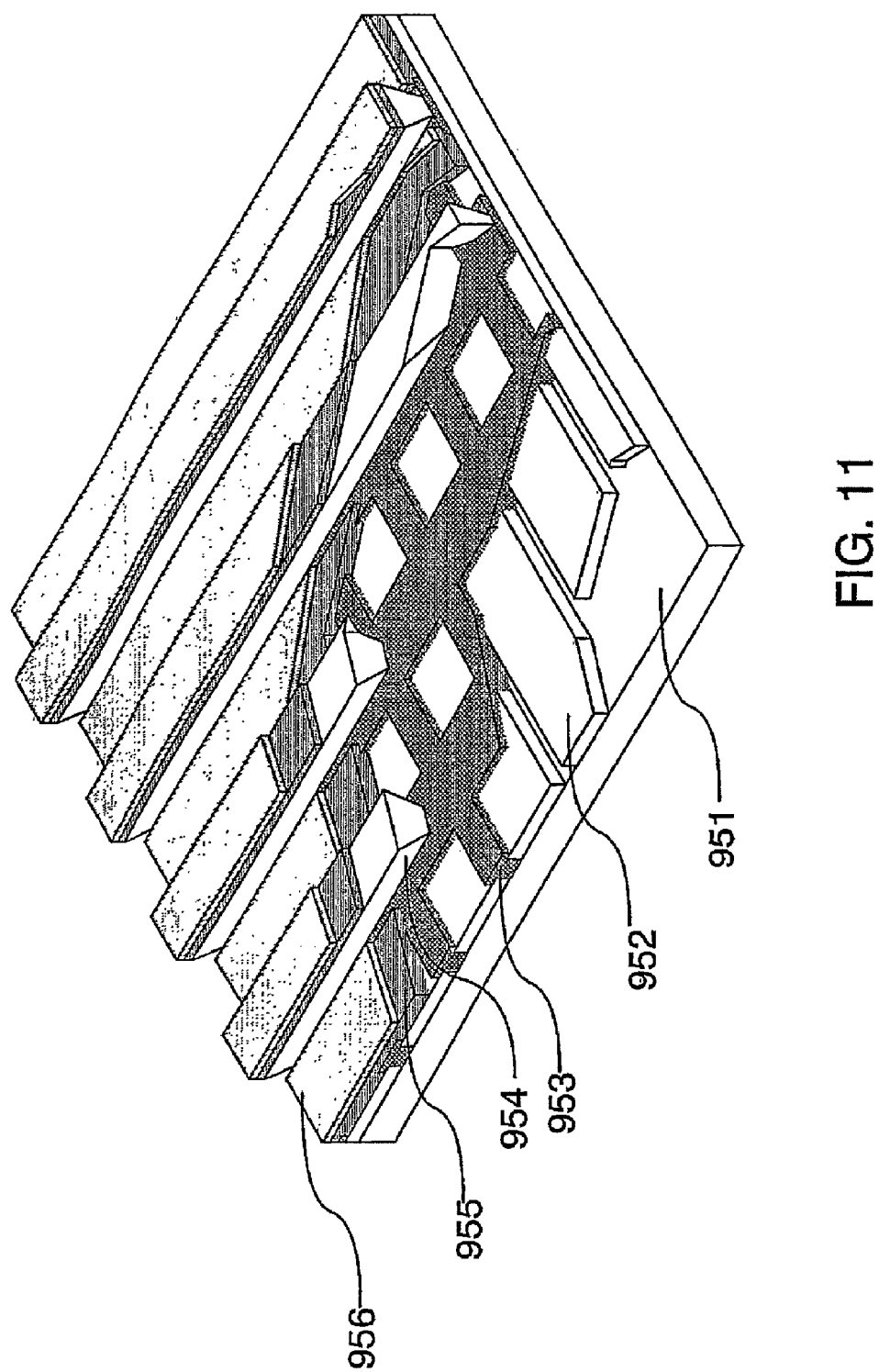
FIG. 11 is a perspective view of a light-emitting device to which the present invention is applied.

As set forth above, an active light-emitting device in which driving of a light-emitting element is controlled by a transistor is explained in this embodiment mode. However, besides, the present invention may be applied to a passive light-emitting device in which a light-emitting element is driven without providing an element for driving such as a transistor. FIG. 11 shows a perspective view of a passive light-emitting device to which the present invention is applied. In FIG. 11, a layer 955 where a layer containing a light-emitting substance, a layer for generating electrons, and a layer for generating holes are sequentially stacked is provided between an electrode 952 and an electrode 956 over a substrate 951. The end of the electrode 952 is covered with an insulating layer 953. A partition wall layer 954 is provided over the insulating layer 953. The nearer the sidewall of the partition wall layer is to a substrate surface, the narrower the distance between one sidewall and the other sidewall is to have inclination. In other words, a cross section of the partition wall layer 954 in a minor axis is a trapezoid, in which the lower base (a base in the same direction as the face direction of the insulating layer 953 and in contact with the insulating layer 953) is shorter than the upper base (a base in the same direction as the face of the insulating layer 953 and not in contact with the insulating layer 953). Accordingly, defectiveness of a light-emitting element due to static electricity or the like can be prevented by providing the partition wall layer 954. In addition, a passive light-emitting device can also be driven with low power consumption by including a light-emitting element according to the present invention that is operated with a low drive voltage.

Embodiment Mode 8

Since a light-emitting device including a light-emitting element according to the present invention can display favorable images in terms of color, an electronic device capable of providing favorable projected images in terms of color can be obtained by applying the light-emitting device according to the present invention to a display portion of the electronic device.

Figure 10A:
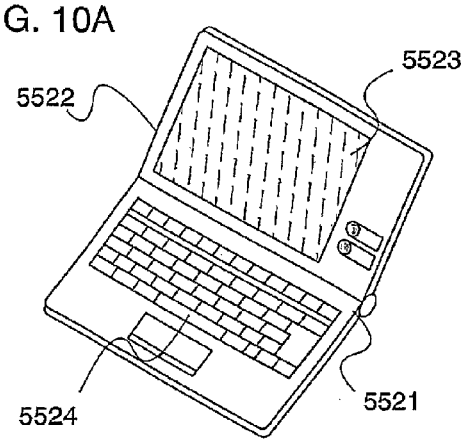
FIGS. 10A to 10C are views of electronic devices to which the present invention is applied.
Figure 10B:
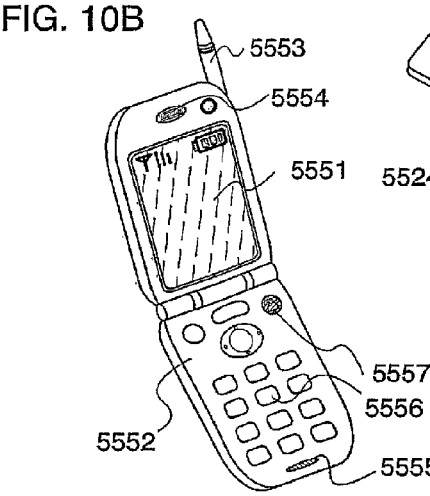
Figure 10C:
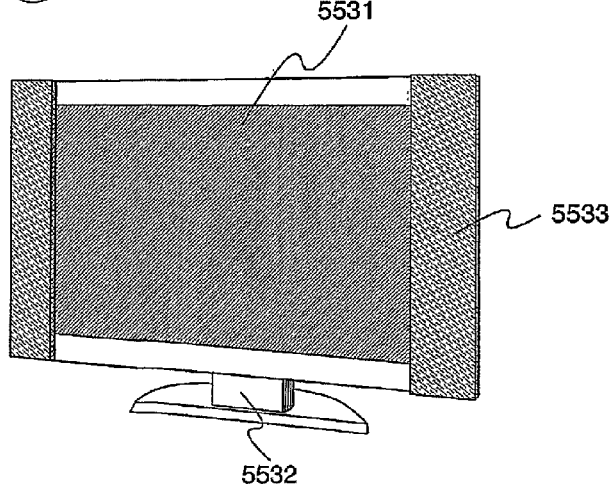

Each of FIGS. 10A to 10C shows one embodiment of an electronic device mounted with a light-emitting device to which the present invention is applied.

FIG. 10A is a personal computer manufactured applying the present invention, which includes a main body 5521, a housing 5522, a display portion 5523, a keyboard 5524, and the like. The personal computer can be achieved by incorporating a light-emitting device having a light-emitting element according to the present invention therein as the display portion.

FIG. 10B is a telephone set manufactured applying the present invention, in which a main body 5552 includes a display portion 5551, an audio output portion 5554, an audio input portion 5555, operation switches 5556 and 5557, an antenna 5553, and the like. The telephone set can be achieved by incorporating a light-emitting device having a light-emitting element according to the present invention therein as the display portion.

FIG. 10C is a television receiver manufactured applying the present invention, which includes a display portion 5531, a housing 5532, speakers 5533, and the like. The television receiver can be achieved by incorporating a light-emitting device having a light-emitting element according to the present invention therein as the display portion.

As set forth above, a light-emitting device according to the present invention is suitable to be used as the display portions of various kinds of electronic devices.

Note that this embodiment mode describes the personal computer, telephone set, and television receiver; however, a light-emitting device having a light-emitting element according to the present invention may also be mounted on a navigation system, a camera, or the like as well.

Embodiment 1

Hereinafter, a synthesis example of an organometallic complex according to the present invention will be explained. However, the present invention is not limited to the organometallic complex of which synthesis example is shown below.

Synthesis Example 1

This synthesis example is a synthesis example of (acetylacetonato)[2,3-bis(4-fluorophenyl)quinoxalinato]platinum (II) (abbreviation: Pt(Fdpq)(acac)) represented by the structural formula (13).
<Step 1: Synthesis of Ligand (HFdpq)>

First, 3.71 g of 4,4'-difluorobenzil and 1.71 g of o-phenylenediamine were stirred on heating in a solvent (200 mL of chloroform) for 6 hours. The reaction solution was cooled to a room temperature, washed with 1 mol/L hydrochloric acid and a saturated aqueous solution of sodium chloride, and dried with magnesium sulfate. The solvent was removed to obtain a ligand 2,3-bis(4-fluorophenyl)quinoxaline) (abbreviation: HFdpq) (pale yellow powder, yield: 99%). A synthetic scheme (b-1) of Step 1 is shown below.

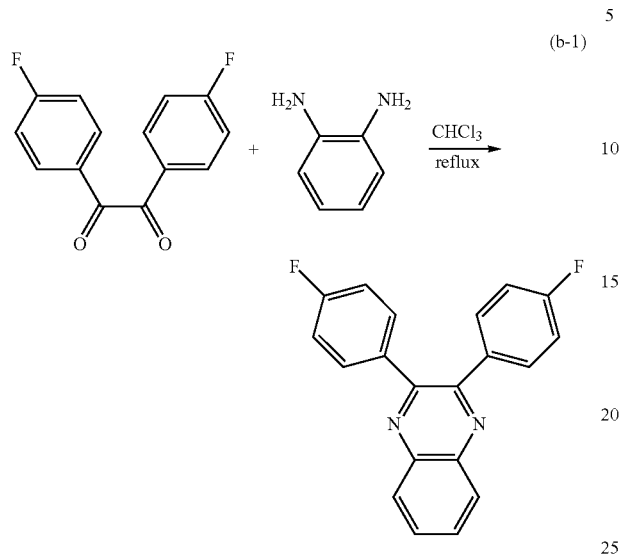

<Step 2: Synthesis of Dimer Complex (abbreviation: [Pt(Fdpq)Cl]$_2$)>

First, with a mixture of 30 mL of 2-ethoxyethanol and 10 mL of water as a solvent, 1.92 g of the ligand 2,3-bis-(4-fluorophenyl)quinoxaline (abbreviation: HFdpq) and 1.00 g of potassium tetrachloroplatinate (K$_2$[PtCl$_4$]) were mixed, and held at 80° C. in a nitrogen atmosphere for 16 hours while heating and stirring to obtain a dimer complex [Pt(Fdpq)Cl]$_2$ (black powder, yield: 85%). A synthetic scheme (b-2) of Step 2 is shown below.

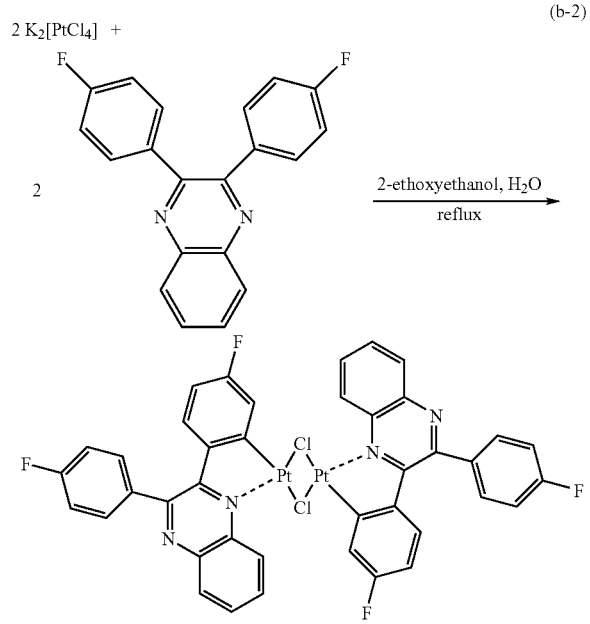

<Step 3: Synthesis of Organometallic Complex (abbreviation: Pt(Fdpq)(acac)) according to the Present Invention>

Further, with 30 mL of 2-ethoxyethanol as a solvent, 1.12 g of the above obtained [Pt(Fdpq)Cl2]$_2$, 0.26 ml of acetylacetone (Hacac), and 1.08 g of sodium carbonate were mixed, and held at reflux in a nitrogen atmosphere for 15 hours to obtain red powder (yield: 3%). A synthetic scheme (b-3) of Step 3 is shown below.

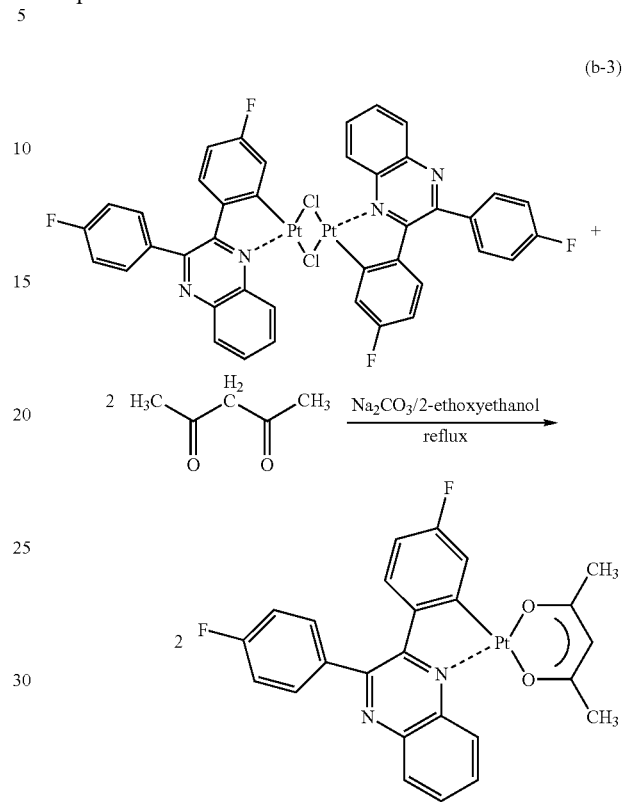

The obtained red powder was analyzed by nuclear magnetic resonance spectroscopy ($^1$H-NMR) and the product was identified to be Pt(Fdpq)(acac) which is one of organometallic complexes according to the present invention. The result of the analysis was as follows.

$^1$H-NMR. δ(CDCl$_3$): 9.29 (d, 1H), 8.05 (d, 1H), 7.72 (m, 4H), 7.37 (dd, 1H), 7.22 (t, 2H), 6.73 (t, 1H), 6.50 (td, 1H), 5.61 (s, 1H), 2.07 (s, 6H)

In addition, measurement of the thermal decomposition temperature T$_d$ of the obtained Pt(Fdpq)(acac) was performed by a Thermogravimetry/Differential Thermal Analysis simultaneous measurement system (from Seiko Instruments Inc., TG/DTA-320) to find T$_d$=266° C., and thus, it was determined that the Pt(Fdpq)(acac) shows favorable heat resistance.

Figure 12:
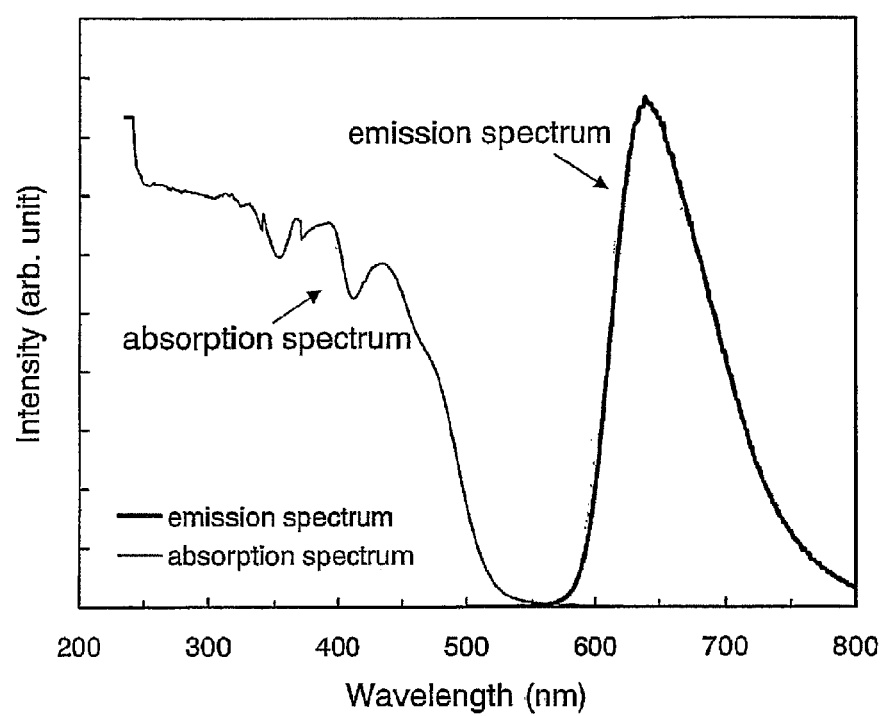
FIG. 12 is a graph showing an emission spectrum and an absorption spectrum of Pt(Fdpq)(acac) according to the present invention.

Moreover, FIG. 12 shows an absorption spectrum of the obtained Pt(Fdpq)(acac) in dichloromethane and an emission spectrum (Photo Luminescence) thereof. Note that the emission spectrum was obtained when light with a wavelength of 482 nm was used as excitation light, where the light with the wavelength of 482 nm was extracted by separating light from a halogen lamp with the use of a slit. In FIG. 12, the horizontal axis indicates a wavelength (nm), and the vertical axis indicates intensity (arb. unit: arbitrary unit). As can be seen from FIG. 12, the organometallic complex Pt(Fdpq)(acac) according to the present invention has absorption peaks at 367 nm, 389 nm, 435 nm, and 470 nm. In addition, the emission spectrum showed an emission peak at 639 nm, and emitted light was visible as red light.

In the case of the obtained Pt(Fdpq)(acac), the several absorption peaks are observed. This is absorption unique to an organometallic complex as in the case of an orthometalated complex or the like, and is believed to correspond to singlet MLCT transition, triplet π-π* transition, triplet MLCT (metal to ligand charge transfer) transition, or the like. In particular, the absorption peak at the longest wavelength side has a broad peak in the visible region, which is considered to be an absorption spectrum unique to triplet MLCT transition. In other words, it is determined that Pt(Fdpq)(acac) is a compound capable of direct photo-excitation to an excited triplet state and intersystem crossing.

Further, a gas including oxygen was injected into a dichloromethane solution including the obtained Pt(Fdpq)(acac), and the emission intensity of Pt(Fdpq)(acac) was examined when the Pt(Fdpq)(acac) with dissolved oxygen was made to be in an emitting state. Furthermore, a gas including argon was injected into a dichloromethane solution including the obtained Pt(Fdpq)(acac), and the emission intensity of Pt(Fdpq)(acac) was examined when the Pt(Fdpq)(acac) with dissolved argon was made to be in an emitting state. From the result, it was determined that luminescence of Pt(Fdpq)(acac) shows the same tendency as luminescence of a phosphorescent substance, where the tendency is that the emission intensity is stronger in the case of dissolved argon than dissolved oxygen. Accordingly, luminescence of Pt(Fdpq)(acac) is believed to be phosphorescence.

Synthesis Example 2

Note that an organometallic complex according to the present invention represented by the structural formula (24) can be obtained by using 2,3-bis(3,5-difluorophenyl)quinoxaline (abbreviation: H(3,5-Fdpq)) as a ligand instead of 2,3-bis(4-fluorophenyl)quinoxaline (abbreviation: HFdpq). H(3,5-Fdpq) can be obtained by such a synthesis method explained below.

Step 1: Synthesis of 3,3',5,5'-tetrafluorobenzyl 3,3',5,5'-tetrafluorobenzyl that is a raw material for a ligand was synthesized as follows. First, 3.16 g of magnesium was suspended in 3 ml of tetrahydrofuran (abbreviation: THF), and a small amount of 1,2-dibromoethane was added. Into this mixture, a solution obtained by adding 130 ml of THF to 25.00 g of 1-bromo-3,5-difluorobenzene was dropped, and the solution was stirred for 1.5 hours under reflux. Next, 9.24 g of 1,4-dimethylpiperazine-2,3-dione was added to the solution cooled to a room temperature, and the solution was stirred for 13 hours under reflux. Further, 200 ml of 10 weight-% hydrochloric acid was added to the solution cooled to a room temperature, and the organic layer was extracted with chloroform. After drying with sodium sulfate, the solvent was condensed. Finally, purification was performed by column chromatography (hexane/dichloromethane system) to obtain 3,3',5,5'-tetrafluorobenzyl (yellow powder, yield: 46%). A synthetic scheme (c-1) is shown below.

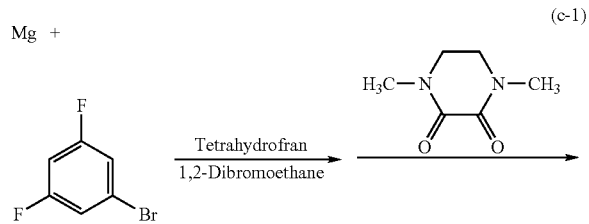

(c-1)

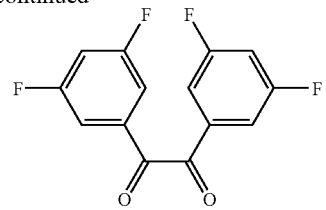

Step 2: Synthesis of Ligand (abbreviation: H(3,5-Fdpq))

A solution was obtained by adding 300 ml of chloroform to 8.32 g of 3,3',5,5'-tetrafluorobenzyl synthesized in Step 1 and 3.19 g of 1,2-phenylenediamine, and the solution was stirred for 10 hours under reflux. The solution cooled to a room temperature was washed with 1 mol/L of hydrochloric acid and then with a saturated aqueous solution of sodium chloride, and dried with sodium sulfate. Then, the solvent was condensed to obtain 2,3-bis(3,5-difluorophenyl)quinoxaline (abbreviation: H(3,5-Fdpq)) (white powder, yield: 98%). A synthetic scheme (c-2) is shown below.

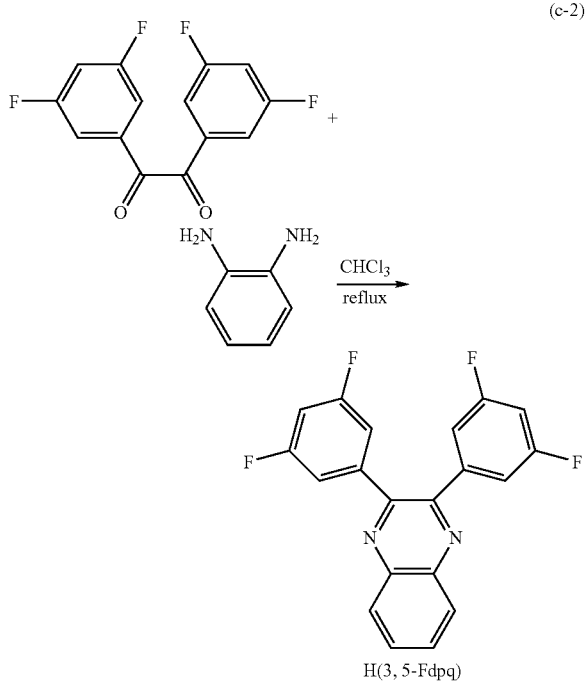

(c-2)

Embodiment 2

This embodiment explains a method for manufacturing a light-emitting element using, as a luminescent substance, Pt(Fdpq)(acac) synthesized in Synthesis Example 1, and an operating characteristic of the light-emitting element with reference to FIGS. 13 to 17.

Figure 13:
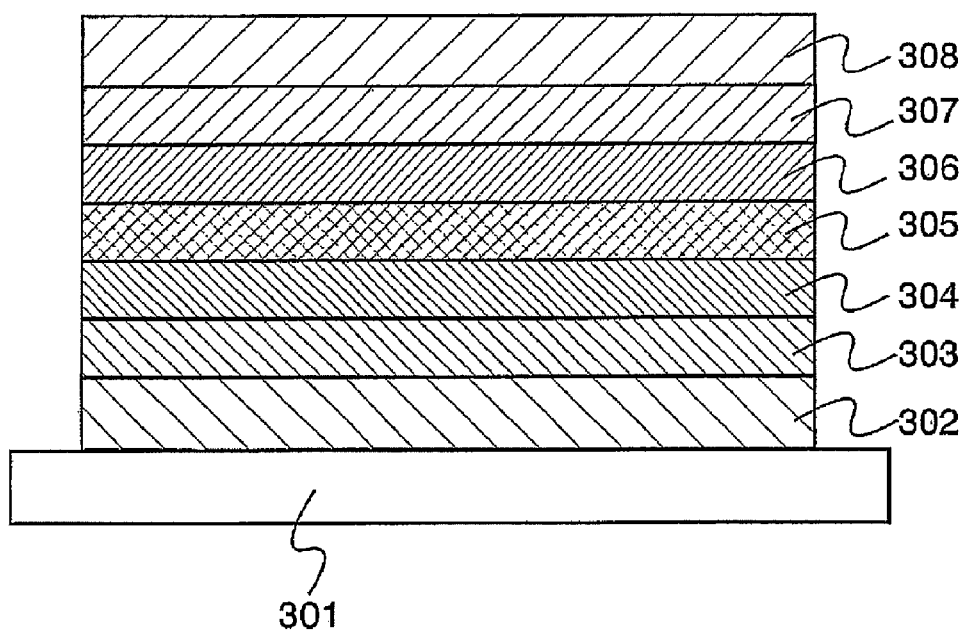
FIG. 13 is a diagram explaining a method for manufacturing a light-emitting element using an organometallic complex according to the present invention.

As shown in FIG. 13, indium tin oxide containing silicon oxide was deposited over a glass substrate 301 by a sputtering method to form a first electrode 302. The film thickness of the first electrode 302 was made to be 110 nm.

Next, the glass substrate 301 where the first electrode 302 is formed was fixed to a holder provided in a vacuum evaporator so that a surface where the first electrode is formed faces downward.

Thereafter, a first layer 303 was formed over the first electrode 302 by a co-evaporation method with the use of NBP and molybdenum trioxide after decompressing inside of the vacuum evaporator to be $1\times10^{-4}$ Pa. The film thickness of the first layer 303 was made to be 50 nm. This first layer 303 is a layer that functions as a hole-generating layer when a light-emitting element is made to operate.

Then, a second layer 304 was formed over the first layer 303 by a vapor deposition method with the use of NPB. The film thickness of the second layer 304 was made to be 10 nm. This second layer 304 is a layer that functions as a hole-transporting layer when a light-emitting element is made to operate.

Thereafter, a third layer 305 containing CBP and Pt(Fdpq)(acac) was formed over the second layer 304 by a co-evaporation method. The film thickness of the third layer 305 was made to be 30 nm, and a mass ratio of CBP to Pt(Fdpq)(acac) was set to be 1:0.05. Accordingly, Pt(Fdpq)(acac) is contained in a layer where CBP is a matrix. This third layer 305 is a layer that functions as a light-emitting layer when a light-emitting element is made to operate. In such a case, Pt(Fdpq)(acac) is referred to as a guest, whereas CBP is referred to as a host.

Subsequently, a fourth layer 306 was formed over the third layer 305 by a vapor deposition method with the use of BCP. The film thickness of the fourth layer 306 was made to be 10 nm. This fourth layer 306 is a layer that functions as an electron-transporting layer when a light-emitting element is made to operate. Note that, as in this embodiment, an electron-transporting layer in the case where ionization potential is higher than a host and where an effect for preventing holes from running through an electrode that functions as a cathode (a second electrode 308 in this embodiment) from a layer that functions as a light-emitting layer (the third layer 305 in this embodiment) is large may be referred particularly as a hole-blocking layer.

Thereafter, a fifth layer 307 containing $Alq_3$ and Li was formed over the fourth layer 306 by a co-evaporation method. The film thickness of the fifth layer 307 was made to be 50 nm. In addition, the mass ratio of $Alq_3$ to Li was set to be 1:0.01. This fifth layer 307 is a layer that functions as an electron-injecting layer when a light-emitting element is made to operate.

Next, the second electrode 308 made from aluminum was formed over the fifth layer 307. The film thickness of the second electrode 308 was made to be 200 nm.

In a light-emitting element manufactured according to the above manner, a current flows when a voltage is applied so that the potential of the first electrode 302 gets higher than the potential of the second electrode 308 and light is emitted when excitation energy is generated after recombining electrons and holes in the third layer 305 that functions as a light-emitting layer and the excited Pt(Fdpq)(acac) returns to a ground state.

In a glove box under a nitrogen atmosphere, a sealing operation was performed so that this light-emitting element is not exposed to an atmosphere. Thereafter, an operating characteristic of the light-emitting element was measured. Note that measurement was performed at a room temperature (an atmosphere kept at 25° C.).

Figure 14:
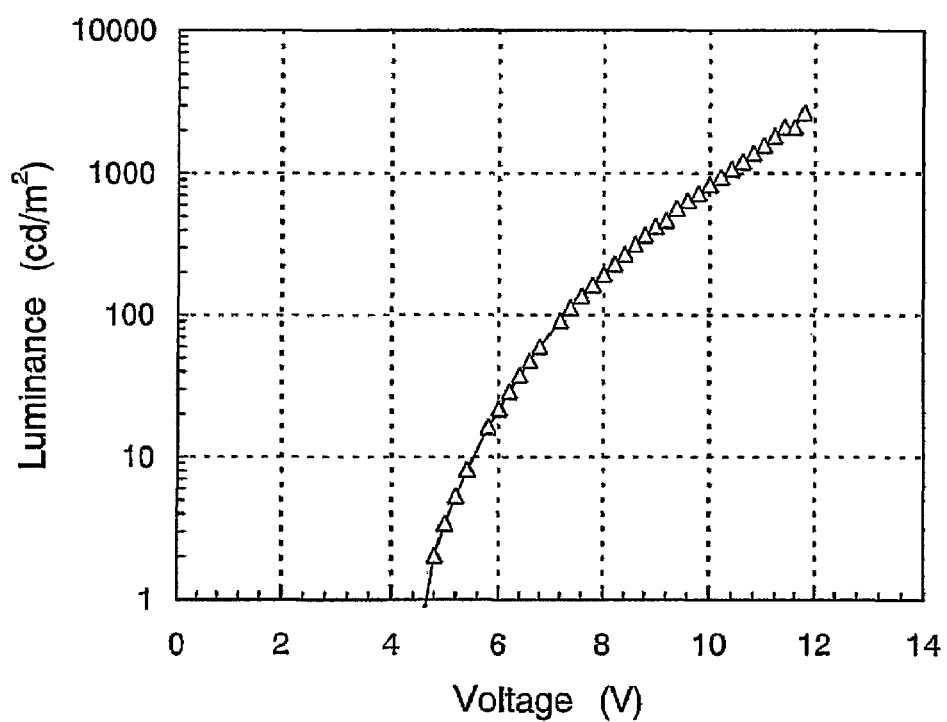
FIG. 14 is a graph showing voltage-luminance characteristics of a light-emitting element using Pt(Fdpq)(acac) obtained in Synthesis Example 1 as a luminescent substance.
Figure 15:
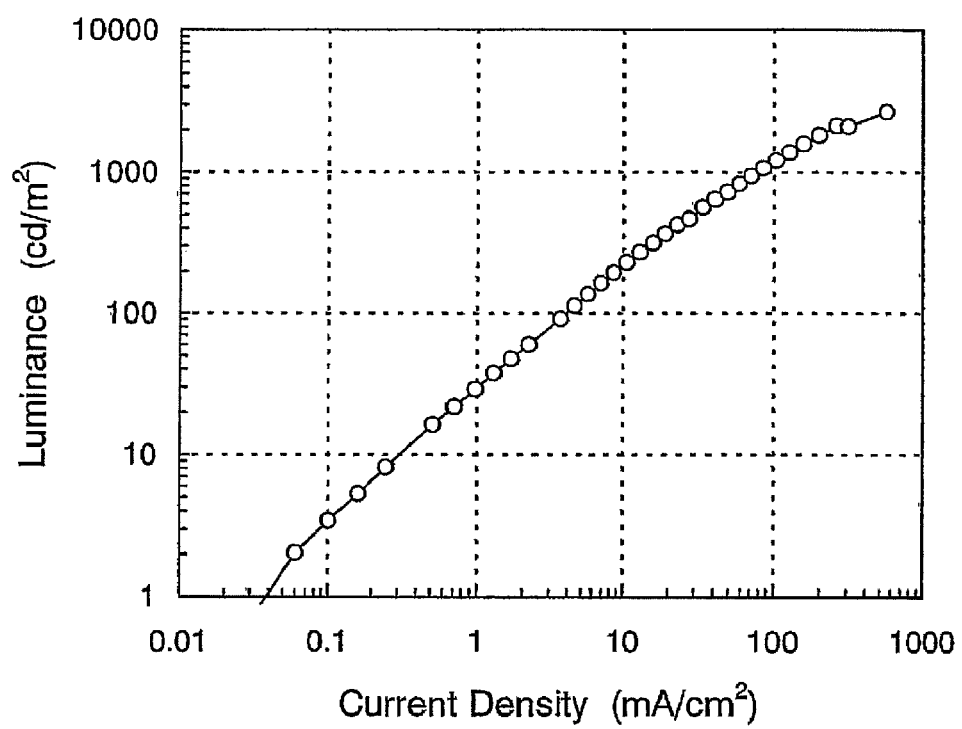
FIG. 15 is a graph showing current density-luminance characteristics of a light-emitting element using Pt(Fdpq)(acac) obtained in Synthesis Example 1 as a luminescent substance.
Figure 16:
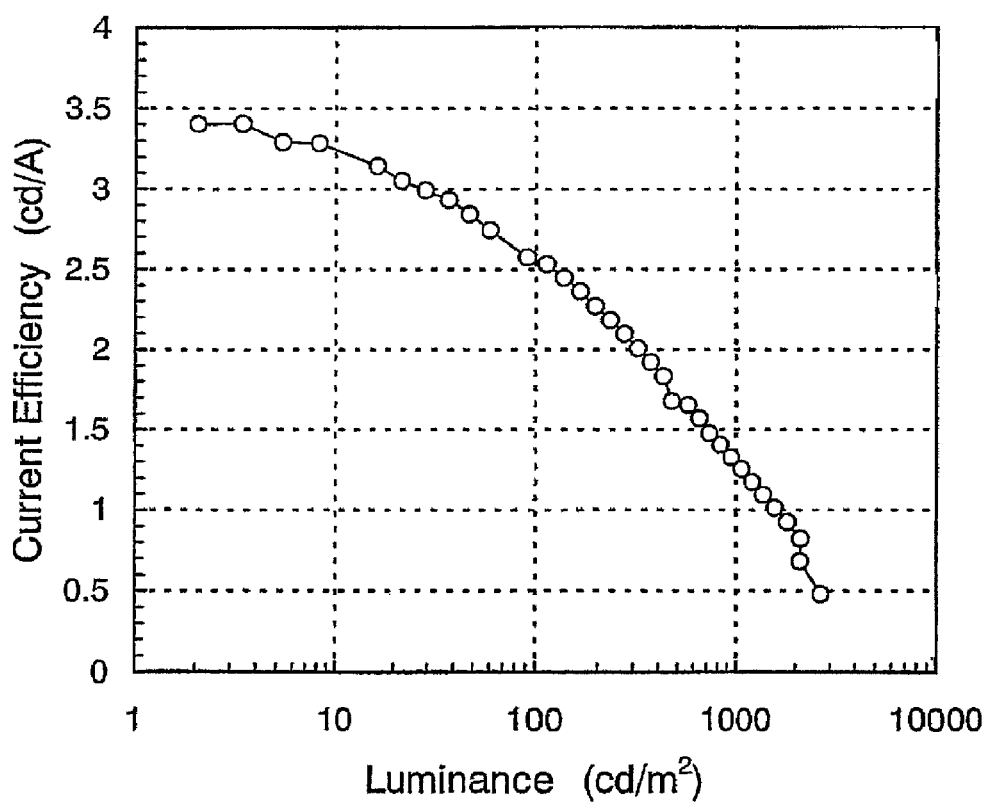
FIG. 16 is a graph showing luminance-current efficiency characteristics of a light-emitting element using Pt(Fdpq)(acac) obtained in Synthesis Example 1 as a luminescent substance.

FIGS. 14 to 16 each show measurement result. FIG. 14 shows a result regarding voltage-luminance characteristics, FIG. 15 shows a result regarding current density-luminance characteristics, and FIG. 16 shows a result regarding luminance-current efficiency. In FIG. 14, a horizontal axis represents a voltage (V), whereas a vertical axis represents a luminance ($cd/m^2$). In addition, in FIG. 15, a horizontal axis represents a current density ($mA/cm^2$), whereas a vertical axis represents a luminance ($cd/m^2$). Further, in FIG. 16, a horizontal axis represents a luminance ($cd/m^2$), whereas a vertical axis represents current efficiency (cd/A). From these results, it was determined that current flows at a current density of 70.9 $mA/cm^2$ when a voltage of 10.2 V is applied to a light-emitting element of this embodiment mode; thus, light emission is obtained at a luminance of 940 $cd/m^2$.

Figure 17:
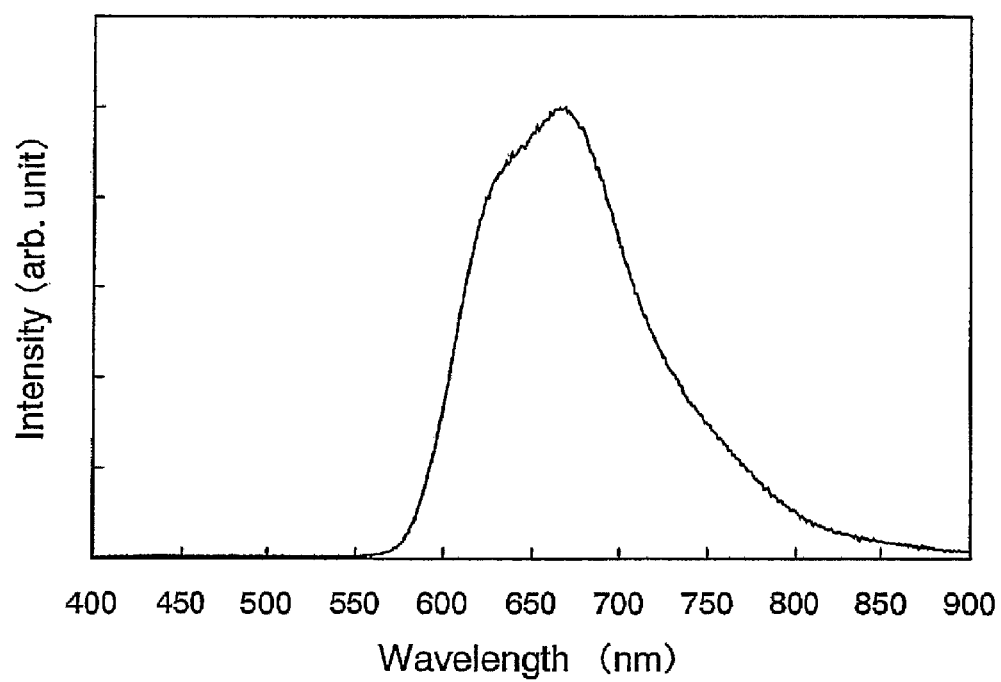
FIG. 17 is a graph showing an emission spectrum of a light-emitting element using Pt(Fdpq)(acac) obtained in Synthesis Example 1 as a luminescent substance.

In addition, FIG. 17 shows an emission spectrum of a light-emitting element manufactured according to this embodiment. In FIG. 17, a horizontal axis represents a wavelength (nm), whereas a vertical axis represents intensity (an arbitrary unit). According to FIG. 17, a light-emitting element in this embodiment has an emission spectrum peak at 672 nm and emits red light derived from Pt(Fdpq)(acac). Further, a chromaticity coordinate in a CIE color system is (x, y)=(0.67, 0.31), from which it is determined that a light-emitting element of this embodiment provides red light.

Explanation of Reference 151: first electrode, 152: second electrode, 161: hole-injecting layer, 162: hole-transporting layer, 163: a light-emitting layer, 164: electron-transporting layer, 165: electron-injecting layer, 751: first electrode, 752: second electrode, 761: electron-injecting layer, 762: electron-transporting layer, 763: first light-emitting layer, 764: energy-generating layer, 765: second light-emitting layer, 766: hole-transporting layer, 767: hole-injecting layer, 771: first electrode, 772: second electrode, 781: electron-injecting layer, 782: electron-transporting layer, 783: first light-emitting layer, 784: hole-transporting layer, 785: first layer, 786: second layer, 787: electron-transporting layer, 788: second light-emitting layer, 789: hole-transporting layer, 790: hole-injecting layer, 181: first electrode, 182: second electrode, 191: hole-transporting layer, 192: hole-injecting layer, 193: light-emitting layer, 194: electron-transporting layer, 195: electron-injecting layer, 301: glass substrate, 302: first electrode, 303: first layer, 304: second layer, 305: third layer, 306: fourth layer, 307: fifth layer, 308: second electrode, 6500: substrate, 6503: FPC (flexible printed circuit), 6504: printed wiring board (PWB), 6511: pixel portion, 6512: source-signal line driver circuit, 6513: writing gate-signal line driver circuit, 6514: erasing gate-signal line driver circuit, 901: first transistor, 902: second transistor, 903: light-emitting element, 911: gate-signal line, 912: source-signal line, 913: writing gate-signal line driver circuit, 914: erasing gate-signal line driver circuit, 915: source-signal line driver circuit, 916: power source, 917: current-supply line, 918: switch, 919: switch, 920: switch, 1001: first transistor, 1002: second transistor, 1003: gate-signal line, 1004: source-signal line, 1005: current-supply line, 1006: electrode, 501: sub-frame, 502: sub-frame, 503: sub-frame, 504: sub-frame, 501*a*: writing period, 501*b*: retention period, 502*a*: writing period, 502*b*: retention period, 503*a*: writing period, 503*b*: retention period, 504*a*: writing period, 504*b*: retention period, 504*c*: erasing period, 504*d*: non-emission period, 10: substrate, 11: transistor, 12: light-emitting element, 13: first electrode, 14: second electrode, 15: layer, 16: interlayer insulating film, 17: wiring, 18: partition layer, 19: interlayer insulating film, 5521: main body, 5522: housing, 5523: display portion, 5524: keyboard, 5551: display portion, 5552: main body, 5553: antenna, 5554: audio output portion, 5555: audio input portion, 5556: operation switch, 5531: display portion, 5532:

housing, 5533: speaker, 951: substrate, 952: electrode, 953: insulating layer, 954: partition layer, 955: layer, and 956: electrode.

The invention claimed is:

1. A light-emitting device comprising:

a pair of electrodes; and a light-emitting layer formed between the pair of electrodes, wherein the light-emitting layer comprises an organometallic complex having a structure represented by a general formula (1),

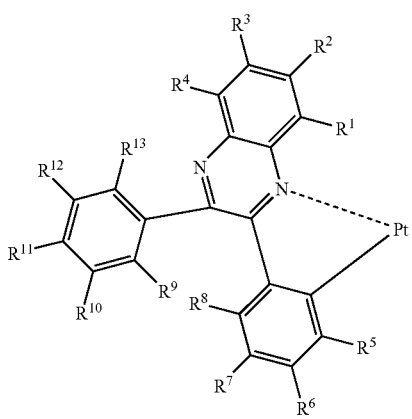

(1)

wherein each of $R^1$ to $R^4$ is any one of hydrogen, a halogen element, an acyl group, an alkyl group, an alkoxyl group, an aryl group, a cyano group, and a heterocyclic group; each of $R^5$ to $R^{13}$ is any one of hydrogen, an acyl group, an alkyl group, an alkoxyl group, an aryl group, a heterocyclic group, and an electron-withdrawing group.

2. A light-emitting device comprising:

a pair of electrodes; and a light-emitting layer formed between the pair of electrodes, wherein the light-emitting layer comprises an organometallic complex having a structure represented by a general formula (2),

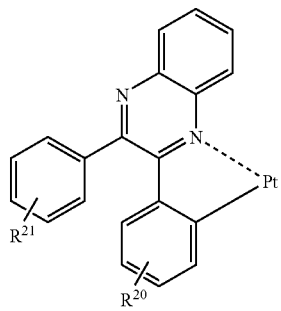

(2)

wherein each of $R^{20}$ and $R^{21}$ is any one of hydrogen, an acyl group, an alkyl group, an alkoxyl group, an aryl group, a heterocyclic group, and an electron-withdrawing group.

3. A light-emitting device comprising:

a pair of electrodes; and a light-emitting layer formed between the pair of electrodes, wherein the light-emitting layer comprises an organometallic complex represented by a general formula (3):

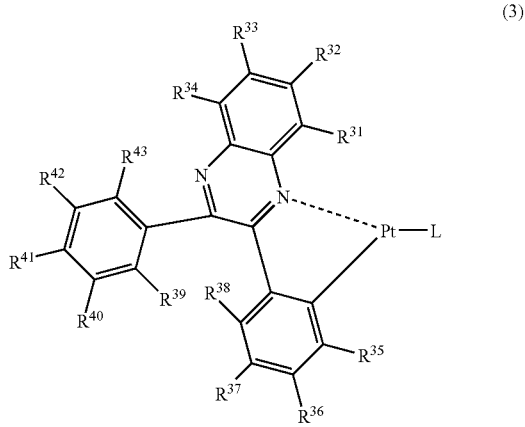

(3)

wherein each of $R^{31}$ to $R^{34}$ is any one of hydrogen, a halogen element, an acyl group, an alkyl group, an alkoxyl group, an aryl group, a cyano group, and a heterocyclic group; each of $R^{35}$ to $R^{43}$ is any one of hydrogen, an acyl group, an alkyl group, an alkoxyl group, an aryl group, a heterocyclic group, and an electron-withdrawing group, and L represents a monoanionic ligand.

4. A light-emitting device according to claim 3, wherein the L is a ligand represented by any one of structural formulas (5) to (11),

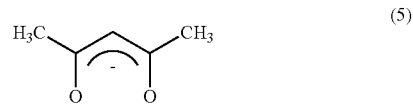

(5)

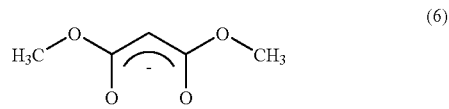

(6)

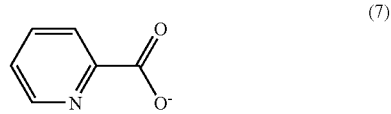

(7)

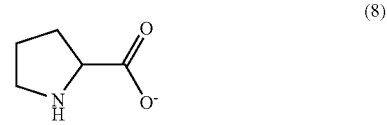

(8)

(9)

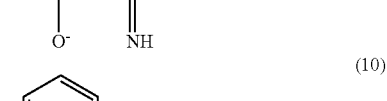

(10)

5. A light-emitting device comprising:

a pair of electrodes; and a light-emitting layer formed between the pair of electrodes, wherein the light-emitting layer comprises an organometallic complex represented by a general formula (4):

(4)

wherein each of $R^{51}$ and $R^{52}$ is any one of hydrogen, an acyl group, an alkyl group, an alkoxyl group, an aryl group, a heterocyclic group, and an electron-withdrawing group, and L represents a monoanionic ligand.

6. A light-emitting device according to claim 5, wherein the L is a ligand represented by any one of structural formulas (5) to (11), (5)

(6)

(7)

(8)

(9)

(10)

(11)

7. A light-emitting device comprising:

a pair of electrodes; and a light-emitting layer formed between the pair of electrodes, wherein the light-emitting layer comprises an organometallic complex represented by a general formula (13):

(13)

8. An electronic device comprising:

a light-emitting device in a display portion, the light-emitting device comprises a light-emitting layer formed between a pair of electrodes, wherein the light-emitting layer comprises an organometallic complex having a structure represented by a general formula (1), (1)

wherein each of $R^1$ to $R^4$ is any one of hydrogen, a halogen element, an acyl group, an alkyl group, an alkoxyl group, an aryl group, a cyano group, and a heterocyclic group;

each of $R^5$ to $R^{13}$ is any one of hydrogen, an acyl group, an alkyl group, an alkoxyl group, an aryl group, a heterocyclic group, and an electron-withdrawing group.

9. An electronic device comprising:

a light-emitting device in a display portion, the light-emitting device comprises a light-emitting layer formed between a pair of electrodes, wherein the light-emitting layer comprises an organometallic complex having a structure represented by a general formula (2),

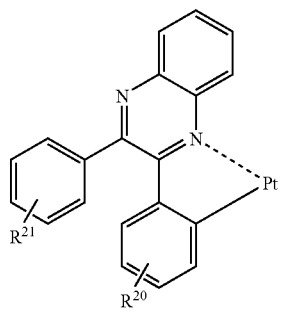
(2)

wherein each of $R^{20}$ and $R^{21}$ is any one of hydrogen, an acyl group, an alkyl group, an alkoxyl group, an aryl group, a heterocyclic group, and an electron-withdrawing group.

10. An electronic device comprising:

a light-emitting device in a display portion, the light-emitting device comprises a light-emitting layer formed between a pair of electrodes, wherein the light-emitting layer comprises an organometallic complex represented by a general formula (3),

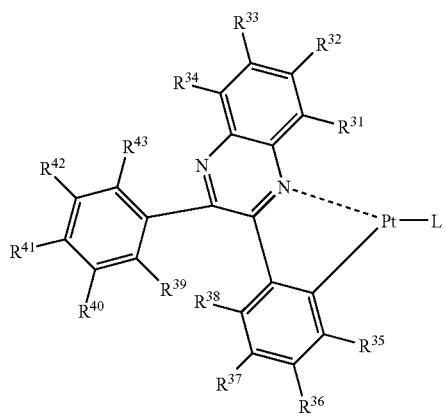
(3)

wherein each of $R^{31}$ to $R^{34}$ is any one of hydrogen, a halogen element, an acyl group, an alkyl group, an alkoxyl group, an aryl group, a cyano group, and a heterocyclic group; each of $R^{35}$ to $R^{43}$ is any one of hydrogen, an acyl group, an alkyl group, an alkoxyl group, an aryl group, a heterocyclic group, and an electron-withdrawing group, and L represents a monoanionic ligand.

11. An electronic device according to claim 10, wherein the L is a ligand represented by any one of structural formulas (5) to (11),

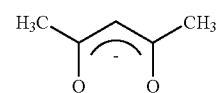
(5)

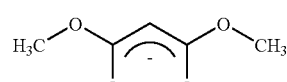
(6)

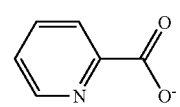
(7)

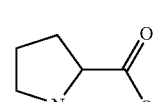
(8)

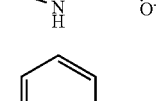
(9)

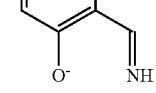
(10)

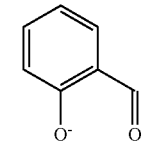
(11)

12. An electronic device comprising:

a light-emitting device in a display portion, the light-emitting device comprises a light-emitting layer formed between a pair of electrodes, wherein the light-emitting layer comprises an organometallic complex represented by a general formula (4),

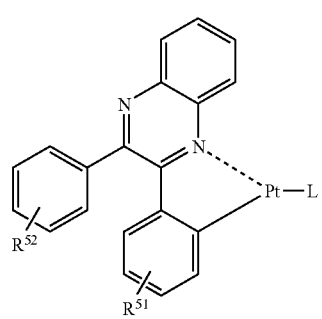
(4)

wherein each of $R^{51}$ and $R^{52}$ is any one of hydrogen, an acyl group, an alkyl group, an alkoxyl group, an aryl group, a heterocyclic group, and an electron-withdrawing group, and L represents a monoanionic ligand.

13. An electronic device according to claim 12, wherein the L is a ligand represented by any one of structural formulas (5) to (11),

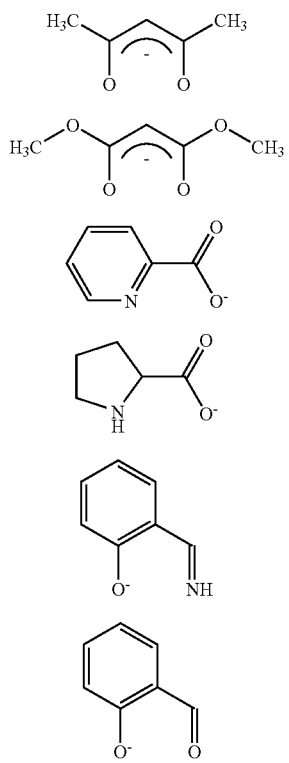

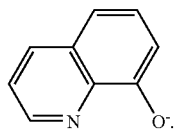

14. An electronic device comprising:
   a light-emitting device in a display portion,
   the light-emitting device comprises a light-emitting layer formed between a pair of electrodes,
   wherein the light-emitting layer comprises an organometallic complex represented by a general formula (13),

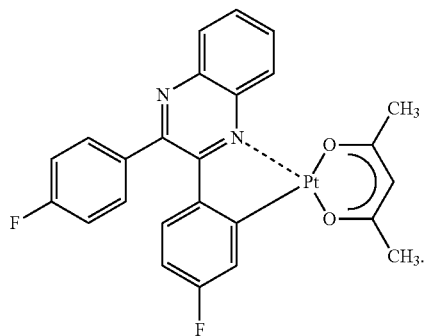

* * * * *